United States Patent [19]
Kröger et al.

[11] Patent Number: 6,066,502
[45] Date of Patent: *May 23, 2000

[54] ENDOTHELIN CONVERTING ENZYME (ECE)

[75] Inventors: Burkhard Kröger, Limburgerhof; Harald Seulberger, Dossenheim; Thomas Meyer, Speyer; Martin Schmidt, Bensheim; Elard Jacob, Eisenberg; Rainer Otter, Sandhausen; Thomas Subkowski, Mutterstadt; Heinz Hillen, Hassloch, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/646,273
[22] PCT Filed: Nov. 10, 1994
[86] PCT No.: PCT/EP94/03706
  § 371 Date: May 16, 1996
  § 102(e) Date: May 16, 1996
[87] PCT Pub. No.: WO95/14095
  PCT Pub. Date: May 26, 1995

[30] Foreign Application Priority Data

Nov. 16, 1993 [DE] Germany .............................. 43 39 100
Feb. 7, 1994 [DE] Germany .............................. 44 03 665
Apr. 12, 1994 [DE] Germany .............................. 44 12 372

[51] Int. Cl.[7] .............................. C12N 15/09; C12N 9/00; C12P 21/06; C07H 21/04
[52] U.S. Cl. .......................... 435/455; 435/440; 435/69.1; 435/183; 536/23.1; 536/23.5
[58] Field of Search .......................... 530/350; 536/23.1, 536/23.5; 435/212, 219, 226, 183, 69.1, 440, 455

[56] References Cited

FOREIGN PATENT DOCUMENTS

WO 92/13944   8/1992   WIPO .

OTHER PUBLICATIONS

Shipp et al. Molecular cloning of the common acute lymphoblastic leukemia antigen (CALLA) identifies a type II integral membrane protein. PNAS, vol. 85, pp. 4819–4823, Jul. 1988.
Opgenorth et al. Endothelian–converting enzymes. FASEB Journal, vol. 6, No. 9, pp. 2653–2659, Jun. 1992.
J. Of Bio. Chem., vol. 269, No. 28, Jul. 199, pp. 18275–18278, 1994.
J. of Bio. Chem., vol. 268, No. 35, Dec. 15, pp. 26759–26766, 1993.
Bio. and Biophysical Comm., vol. 203,. No. 3, 1994, pp. 1417–1422.
Pharmaceutical Res., vol. 5, No. 9, 1988.
Bio. and Biophysical Res. Comm., vol 171, No. 3, 1990, Sep. 28, 1990, pp. 1192–1198.
Bioorganic & Med. Chem. Lt. vol. 3, No. 10, 1993.
Bioscience, Biotech. and Biochem., vol. 57, Nov. 1993, pp. 1944–1945.
Derwent, JP 4 120 593, Abst.
Jor. of Bio. Chem. vol. 268, No. 28, Oct. 5, 1993, pp. 21394–21398.

*Primary Examiner*—Jasemine C. Chambers
*Assistant Examiner*—Deborah J. R. Clark
*Attorney, Agent, or Firm*—Keil & Weinkauf

[57] ABSTRACT

The invention relates to endothelin-converting enzymes containing the polypeptide sequence described in SEQ. ID. NO. 30 or SEQ. ID. NO. 36 or functional fragments thereof, genes which code for such enzymes, and processes for producing the said enzymes and the use thereof.

4 Claims, No Drawings

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Xaa Xaa Pro Asn Ala Leu Asn Phe Gly Gly Ile Gly Val Val Gly
1               5                   10                  15

His Glu Leu Thr His Ala Phe
            20

(2) INFORMATION FOR SEQ ID NO: 2:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Xaa Tyr Xaa Lys Xaa Gly Asn Leu Arg Pro
1               5                   10

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Xaa Ile Ala Xaa Glu Thr Xaa Xaa Glu Ile
1               5                   10

(2) INFORMATION FOR SEQ ID NO: 4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Xaa Pro Glu Phe Leu Leu Glu Gly Leu Ile Thr Asp Pro
1               5                   10

(2) INFORMATION FOR SEQ ID NO: 5:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Xaa Gln Ala Glu Asn Val Ile Gln Val Xaa Gln
 1               5                  10
```

(2) INFORMATION FOR SEQ ID NO: 6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Val Glu Ile Val Phe Pro Xaa Gly Ile Leu Gln Ala Pro Phe Tyr Thr
 1               5                  10                  15
```

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 7:

GGSCAYGARY TNACNCAYGC                                      20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 8:

GARATYGTST TYCCYGCYGG                                      20

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 9:

ATYCTSCAGG CYCCYTTYTA YAC                                 23

(2) INFORMATION FOR SEQ ID NO: 10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 10:

CGAGGGGGAT GGTCGACGGA AGCGACCTTT TTTTTTTTTT TTTTT              45

(2) INFORMATION FOR SEQ ID NO: 11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 11:

```
CGAGGGGGAT GGTCGACGG                                              19
```

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 12:

```
GATGGTCGAC GGAAGCGACC                                             20
```

(2) INFORMATION FOR SEQ ID NO:13:

(i) SEQUENCE CHARACTERISTICS:
        (A) LENGTH: 570 base pairs
        (B) TYPE: nucleic acid
        (C) STRANDEDNESS: single
        (D) TOPOLOGY: linear (ii) MOLECULE TYPE: cDNA for mRNA (xi) SEQUENCE DESCRIPTION: SEQ ID NO: 13:

```
ATC CTG CAG GCG CCA TTC TAC ACC CGC TCT TCA CCC AAT GCC TTA AAC        48
Ile Leu Gln Ala Pro Phe Tyr Thr Arg Ser Ser Pro Asn Ala Leu Asn
 1               5                  10                  15

TTC GGC GGC ATC GGC GTC GTC GTG GGC CAC GAG CTG ACT CAT GCT TTT        96
Phe Gly Gly Ile Gly Val Val Val Gly His Glu Leu Thr His Ala Phe
             20                  25                  30

GAT GAT CAA GGC CGA GAG TAC GAC AAG GAT GGG AAC CTC CGG CCC TGG       144
Asp Asp Gln Gly Arg Glu Tyr Asp Lys Asp Gly Asn Leu Arg Pro Trp
         35                  40                  45

TGG AAG AAC TCG TCC GTG GAG GCG TTC AAG CAG CAG ACC GCG TGC ATG       192
Trp Lys Asn Ser Ser Val Glu Ala Phe Lys Gln Gln Thr Ala Cys Met
     50                  55                  60

GTG GAG CAG TAC GGC AAC TAT AGC GTG AAC GGG GAG CCG GTG AAC GGC       240
Val Glu Gln Tyr Gly Asn Tyr Ser Val Asn Gly Glu Pro Val Asn Gly
 65                  70                  75                  80

CGG CAC ACC CTC GGC GAA AAC ATC GCC GAC AAC GGG GGC CTC AAG GCG       288
Arg His Thr Leu Gly Glu Asn Ile Ala Asp Asn Gly Gly Leu Lys Ala
                 85                  90                  95

GCC TAT CGG GCC TAC CAG AAC TGG GTC AAG AAG AAT GGG GCT GAG CAG       336
Ala Tyr Arg Ala Tyr Gln Asn Trp Val Lys Lys Asn Gly Ala Glu Gln
            100                 105                 110

ACA CTG CCC ACC CTG GGT CTC ACC AAC AAC CAG CTC TTC TTC CTG AGT       384
Thr Leu Pro Thr Leu Gly Leu Thr Asn Asn Gln Leu Phe Phe Leu Ser
        115                 120                 125

TTT GCA CAG GTC TGG TGT TCC GTC CGC ACC CCC GAG AGT TCG CAC GAA       432
Phe Ala Gln Val Trp Cys Ser Val Arg Thr Pro Glu Ser Ser His Glu
    130                 135                 140
```

```
GGT CTC ATC ACC GAT CCC CAC AGC CCC TCC CGC TTC CGG GTC ATC GGC        480
Gly Leu Ile Thr Asp Pro His Ser Pro Ser Arg Phe Arg Val Ile Gly
145                 150                 155                 160

TCC ATC TCC AAC TCC AAG GAG TTC TCG GAA CAC TTC CAC TGC CCG CCC        528
Ser Ile Ser Asn Ser Lys Glu Phe Ser Glu His Phe His Cys Pro Pro
                165                 170                 175

GGC TCA CCC ATG AAC CCG CAT CAC AAG TGT GAA GTC TGG TGA                570
Gly Ser Pro Met Asn Pro His His Lys Cys Glu Val Trp
            180                 185
```

(2) INFORMATION FOR SEQ ID NO: 14:

(i) SEQUENCE CHARACTERISTICS:
        (A) LENGTH: 189 amino acids
        (B) TYPE: amino acid
        (D) TOPOLOGY: linear (ii) MOLECULE TYPE: protein (xi) SEQUENCE DESCRIPTION: SEQ ID NO: 14:

```
Ile Leu Gln Ala Pro Phe Tyr Thr Arg Ser Ser Pro Asn Ala Leu Asn
 1               5                  10                  15

Phe Gly Gly Ile Gly Val Val Gly His Glu Leu Thr His Ala Phe
            20                  25                  30

Asp Asp Gln Gly Arg Glu Tyr Asp Lys Asp Gly Asn Leu Arg Pro Trp
            35                  40                  45

Trp Lys Asn Ser Ser Val Glu Ala Phe Lys Gln Thr Ala Cys Met
 50                  55                  60

Val Glu Gln Tyr Gly Asn Tyr Ser Val Asn Gly Glu Pro Val Asn Gly
 65                  70                  75                  80

Arg His Thr Leu Gly Glu Asn Ile Ala Asp Asn Gly Gly Leu Lys Ala
                85                  90                  95

Ala Tyr Arg Ala Tyr Gln Asn Trp Val Lys Lys Asn Gly Ala Glu Gln
                100                 105                 110

Thr Leu Pro Thr Leu Gly Leu Thr Asn Asn Gln Leu Phe Phe Leu Ser
                115                 120                 125

Phe Ala Gln Val Trp Cys Ser Val Arg Thr Pro Glu Ser Ser His Glu
            130                 135                 140

Gly Leu Ile Thr Asp Pro His Ser Pro Ser Arg Phe Arg Val Ile Gly
145                 150                 155                 160

Ser Ile Ser Asn Ser Lys Glu Phe Ser Glu His Phe His Cys Pro Pro
                165                 170                 175

Gly Ser Pro Met Asn Pro His His Lys Cys Glu Val Trp
            180                 185
```

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 15:

```
GAGAGAGAGT CGACGGTACC NNNNNNN                                           27
```

(2) INFORMATION FOR SEQ ID NO: 16:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 16:

CGGCCCTGGT GGAAGAACTC G                                              21

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 17:

TGCGGACGGA ACACCAGACC T                                              21

(2) INFORMATION FOR SEQ ID NO: 18:

(i) SEQUENCE CHARACTERISTICS:
        (A) LENGTH: 1703 base pairs
        (B) TYPE: nucleic acid
        (C) STRANDEDNESS: single
        (D) TOPOLOGY: linear (ii) MOLECULE TYPE: cDNA for mRNA (xi) SEQUENCE DESCRIPTION: SEQ ID NO: 18:

```
T   GGC CAC TCG CGC TGG GGG ACC TTC AGC AAC CTC TGG GAA CAC AAC       46
    Gly His Ser Arg Trp Gly Thr Phe Ser Asn Leu Trp Glu His Asn
     1               5                  10                  15

CAA GCC ATC ATC AAG CAC CTC CTT GAA AAC TCC ACG GCC AGC GTG AGC       94
Gln Ala Ile Ile Lys His Leu Leu Glu Asn Ser Thr Ala Ser Val Ser
                 20                  25                  30

GAG GCA GAG AGG AAG GAC CAG GAG TAC TAC CGA GCC TGC ATG AAC GAA      142
Glu Ala Glu Arg Lys Asp Gln Glu Tyr Tyr Arg Ala Cys Met Asn Glu
             35                  40                  45

ACC AGG ATT GAG GAG CTC AAG GCC AAA CCC CTG ATG GAG CTC ATT GAG      190
Thr Arg Ile Glu Glu Leu Lys Ala Lys Pro Leu Met Glu Leu Ile Glu
         50                  55                  60

AAG CTC GGC GGC TGG AAC ATC ACG GGG CCC TGG GAC AAG GAC AAC TTC      238
Lys Leu Gly Gly Trp Asn Ile Thr Gly Pro Trp Asp Lys Asp Asn Phe
 65                  70                  75

CAG GAC ACC CTG CAG GTG GTC ACA TCC CAC TAC CAC ACC TCC CCC TTC      286
Gln Asp Thr Leu Gln Val Val Thr Ser His Tyr His Thr Ser Pro Phe
 80                  85                  90                  95

TTC TCC GTC TAC GTC AGT GCC GAC TCC AAG AAT TCC AAC AGC AAC GTG      334
Phe Ser Val Tyr Val Ser Ala Asp Ser Lys Asn Ser Asn Ser Asn Val
                100                 105                 110

ATC CAA GTG GAC CAG TCT GGC CTG GGC TTA CCC TCA AGA GAT TAT TAC      382
Ile Gln Val Asp Gln Ser Gly Leu Gly Leu Pro Ser Arg Asp Tyr Tyr
            115                 120                 125

CTG AAC AAA ACC GAG AAT GAG AAG GTG CTG ACG GGA TAC CTG AAC TAC      430
Leu Asn Lys Thr Glu Asn Glu Lys Val Leu Thr Gly Tyr Leu Asn Tyr
        130                 135                 140

ATG GTC CAG CTG GGG AAG CTG CTG GGA GGA GGG GCC GAG GAC ACC ATC      478
Met Val Gln Leu Gly Lys Leu Leu Gly Gly Gly Ala Glu Asp Thr Ile
```

```
                 145                 150                 155
CGG CCC CAG ATG CAG CAG ATC CTG GAC TTT GAG ACG GCG CTG GCC AAC         526
Arg Pro Gln Met Gln Gln Ile Leu Asp Phe Glu Thr Ala Leu Ala Asn
160                 165                 170                 175

ATC ACC ATC CCC CAG GAG AAG CGC CGG GAC GAG GAA CTC ATC TAC CAC         574
Ile Thr Ile Pro Gln Glu Lys Arg Arg Asp Glu Glu Leu Ile Tyr His
                    180                 185                 190

AAA GTG ACG GCG GCT GAG TTG CAG ACC TTG GCG CCC GCC ATC AAC TGG         622
Lys Val Thr Ala Ala Glu Leu Gln Thr Leu Ala Pro Ala Ile Asn Trp
                195                 200                 205

CTG CCC TTC CTC AAC ACC ATC TTC TAC CCC GTG GAG ATC AAT GAA TCA         670
Leu Pro Phe Leu Asn Thr Ile Phe Tyr Pro Val Glu Ile Asn Glu Ser
            210                 215                 220

GAG CCT ATT GTC ATC TAC GAC AAA GAA TAC CTG AGC AAG GTC TCC ACC         718
Glu Pro Ile Val Ile Tyr Asp Lys Glu Tyr Leu Ser Lys Val Ser Thr
        225                 230                 235

CTC ATC AAC AGC ACA GAC AAA TGC CTG CTG AAC AAC TAC ATG ATC TGG         766
Leu Ile Asn Ser Thr Asp Lys Cys Leu Leu Asn Asn Tyr Met Ile Trp
240                 245                 250                 255

AAC CTG GTA CGG AAG ACG AGC TCC TTC CTC GAT CAG CGC TTC CAG GAC         814
Asn Leu Val Arg Lys Thr Ser Ser Phe Leu Asp Gln Arg Phe Gln Asp
                    260                 265                 270

GCC GAC GAG AAG TTC ATG GAA GTC ATG TAT GGG ACC AAG AAG ACG TGT         862
Ala Asp Glu Lys Phe Met Glu Val Met Tyr Gly Thr Lys Lys Thr Cys
                275                 280                 285

CTT CCC CGC TGG AAG TTT TGT GTG AGT GAT ACA GAG AAC ACC TTG GGC         910
Leu Pro Arg Trp Lys Phe Cys Val Ser Asp Thr Glu Asn Thr Leu Gly
            290                 295                 300

TTC GCC CTG GGC CCC ATG TTC GTC AAA GCG ACC TTC GCT GAG GAC AGC         958
Phe Ala Leu Gly Pro Met Phe Val Lys Ala Thr Phe Ala Glu Asp Ser
        305                 310                 315

AAG AAC ATA GCC AGC GAG ATC ATC CTG GAG ATC AAG AAG GCG TTT GAA        1006
Lys Asn Ile Ala Ser Glu Ile Ile Leu Glu Ile Lys Lys Ala Phe Glu
320                 325                 330                 335

GAG AGC CTG AGC ACC CTG AAG TGG ATG GAT GAA GAT ACT CGG AAA TCG        1054
Glu Ser Leu Ser Thr Leu Lys Trp Met Asp Glu Asp Thr Arg Lys Ser
                    340                 345                 350

GCC AAG GAA AAG GCG GAC GCG ATC TAC AAC ATG ATA GGC TAC CCC AAC        1102
Ala Lys Glu Lys Ala Asp Ala Ile Tyr Asn Met Ile Gly Tyr Pro Asn
                355                 360                 365

TTT ATC ATG GAC CCC AAG GAG CTG GAC AAA GTG TTC AAT GAC TAC ACC        1150
Phe Ile Met Asp Pro Lys Glu Leu Asp Lys Val Phe Asn Asp Tyr Thr
            370                 375                 380

GCT GTG CCA GAC CTC TAC TTC GAG AAC GCC ATG CGG TTT TTC AAC TTC        1198
Ala Val Pro Asp Leu Tyr Phe Glu Asn Ala Met Arg Phe Phe Asn Phe
        385                 390                 395

TCC TGG AGG GTC ACT GCC GAC CAG CTC CGG AAA GCG CCC AAC AGA GAT        1246
Ser Trp Arg Val Thr Ala Asp Gln Leu Arg Lys Ala Pro Asn Arg Asp
400                 405                 410                 415

CAG TGG AGC ATG ACC CCG CCC ATG GTG AAC GCC TAC TAC TCG CCC ACC        1294
Gln Trp Ser Met Thr Pro Pro Met Val Asn Ala Tyr Tyr Ser Pro Thr
                    420                 425                 430

AAG AAC GAG ATC GTG TTT CCG GCC GGA ATC CTG CAG GCG CCA TTC TAC        1342
Lys Asn Glu Ile Val Phe Pro Ala Gly Ile Leu Gln Ala Pro Phe Tyr
                435                 440                 445

ACC CGC TCT TCA CCC AAT GCC TTA AAC TTC GGC GGC ATC GGC GTC GTC        1390
Thr Arg Ser Ser Pro Asn Ala Leu Asn Phe Gly Gly Ile Gly Val Val
            450                 455                 460

GTG GGC CAC GAG CTG ACT CAT GCT TTT GAT GAT CAA GGC CGA GAG TAC        1438
```

```
Val Gly His Glu Leu Thr His Ala Phe Asp Asp Gln Gly Arg Glu Tyr
465                 470                 475

GAC AAG GAT GGG AAC CTC CGG CCC TGG TGG AAG AAC TCG TCC GTG GAG    1486
Asp Lys Asp Gly Asn Leu Arg Pro Trp Trp Lys Asn Ser Ser Val Glu
480                 485                 490                 495

GCG TTC AAG CAG CAG ACC GCG TGC ATG GTG GAG CAG TAC GGC AAC TAT    1534
Ala Phe Lys Gln Gln Thr Ala Cys Met Val Glu Gln Tyr Gly Asn Tyr
                500                 505                 510

AGC GTG AAC GGG GAG CCG GTG AAC GGC CGG CAC ACC CTC GGC GAA AAC    1582
Ser Val Asn Gly Glu Pro Val Asn Gly Arg His Thr Leu Gly Glu Asn
            515                 520                 525

ATC GCC GAC AAC GGG GGC CTC AAG GCG GCC TAT CGG GCC TAC CAG AAC    1630
Ile Ala Asp Asn Gly Gly Leu Lys Ala Ala Tyr Arg Ala Tyr Gln Asn
        530                 535                 540

TGG GTC AAG AAG AAT GGG GCT GAG CAG ACA CTG CCC ACC CTG GGT CTC    1678
Trp Val Lys Lys Asn Gly Ala Glu Gln Thr Leu Pro Thr Leu Gly Leu
545                 550                 555

ACC AAC AAC CAG CTC TTC TTC CTG A                                  1703
Thr Asn Asn Gln Leu Phe Phe Leu
560                 565
```

(2) INFORMATION FOR SEQ ID NO: 19:

(i) SEQUENCE CHARACTERISTICS:
        (A) LENGTH: 567 amino acids
        (B) TYPE: amino acid
        (D) TOPOLOGY: linear (ii) MOLECULE TYPE: protein (xi) SEQUENCE DESCRIPTION: SEQ ID NO: 19:

```
Gly His Ser Arg Trp Gly Thr Phe Ser Asn Leu Trp Glu His Asn Gln
1               5                   10                  15

Ala Ile Ile Lys His Leu Leu Glu Asn Ser Thr Ala Ser Val Ser Glu
            20                  25                  30

Ala Glu Arg Lys Asp Gln Glu Tyr Tyr Arg Ala Cys Met Asn Glu Thr
        35                  40                  45

Arg Ile Glu Glu Leu Lys Ala Lys Pro Leu Met Glu Leu Ile Glu Lys
    50                  55                  60

Leu Gly Gly Trp Asn Ile Thr Gly Pro Trp Asp Lys Asp Asn Phe Gln
65                  70                  75                  80

Asp Thr Leu Gln Val Val Thr Ser His Tyr His Thr Ser Pro Phe Phe
                85                  90                  95

Ser Val Tyr Val Ser Ala Asp Ser Lys Asn Ser Asn Ser Asn Val Ile
            100                 105                 110

Gln Val Asp Gln Ser Gly Leu Gly Leu Pro Ser Arg Asp Tyr Tyr Leu
        115                 120                 125

Asn Lys Thr Glu Asn Glu Lys Val Leu Thr Gly Tyr Leu Asn Tyr Met
    130                 135                 140

Val Gln Leu Gly Lys Leu Leu Gly Gly Ala Glu Asp Thr Ile Arg
145                 150                 155                 160

Pro Gln Met Gln Gln Ile Leu Asp Phe Glu Thr Ala Leu Ala Asn Ile
                165                 170                 175

Thr Ile Pro Gln Glu Lys Arg Arg Asp Glu Glu Leu Ile Tyr His Lys
            180                 185                 190

Val Thr Ala Ala Glu Leu Gln Thr Leu Ala Pro Ala Ile Asn Trp Leu
        195                 200                 205

Pro Phe Leu Asn Thr Ile Phe Tyr Pro Val Glu Ile Asn Glu Ser Glu
```

```
            210                 215                 220
Pro Ile Val Ile Tyr Asp Lys Glu Tyr Leu Ser Lys Val Ser Thr Leu
225                 230                 235                 240

Ile Asn Ser Thr Asp Lys Cys Leu Leu Asn Asn Tyr Met Ile Trp Asn
                245                 250                 255

Leu Val Arg Lys Thr Ser Ser Phe Leu Asp Gln Arg Phe Gln Asp Ala
                260                 265                 270

Asp Glu Lys Phe Met Glu Val Met Tyr Gly Thr Lys Lys Thr Cys Leu
                275                 280                 285

Pro Arg Trp Lys Phe Cys Val Ser Asp Thr Glu Asn Thr Leu Gly Phe
            290                 295                 300

Ala Leu Gly Pro Met Phe Val Lys Ala Thr Phe Ala Glu Asp Ser Lys
305                 310                 315                 320

Asn Ile Ala Ser Glu Ile Ile Leu Glu Ile Lys Lys Ala Phe Glu Glu
                325                 330                 335

Ser Leu Ser Thr Leu Lys Trp Met Asp Glu Asp Thr Arg Lys Ser Ala
                340                 345                 350

Lys Glu Lys Ala Asp Ala Ile Tyr Asn Met Ile Gly Tyr Pro Asn Phe
            355                 360                 365

Ile Met Asp Pro Lys Glu Leu Asp Lys Val Phe Asn Asp Tyr Thr Ala
370                 375                 380

Val Pro Asp Leu Tyr Phe Glu Asn Ala Met Arg Phe Asn Phe Ser
385                 390                 395                 400

Trp Arg Val Thr Ala Asp Gln Leu Arg Lys Ala Pro Asn Arg Asp Gln
                405                 410                 415

Trp Ser Met Thr Pro Pro Met Val Asn Ala Tyr Tyr Ser Pro Thr Lys
                420                 425                 430

Asn Glu Ile Val Phe Pro Ala Gly Ile Leu Gln Ala Pro Phe Tyr Thr
            435                 440                 445

Arg Ser Ser Pro Asn Ala Leu Asn Phe Gly Gly Ile Gly Val Val Val
450                 455                 460

Gly His Glu Leu Thr His Ala Phe Asp Asp Gln Gly Arg Glu Tyr Asp
465                 470                 475                 480

Lys Asp Gly Asn Leu Arg Pro Trp Trp Lys Asn Ser Ser Val Glu Ala
                485                 490                 495

Phe Lys Gln Gln Thr Ala Cys Met Val Glu Gln Tyr Gly Asn Tyr Ser
            500                 505                 510

Val Asn Gly Glu Pro Val Asn Gly Arg His Thr Leu Gly Glu Asn Ile
            515                 520                 525

Ala Asp Asn Gly Gly Leu Lys Ala Ala Tyr Arg Ala Tyr Gln Asn Trp
            530                 535                 540

Val Lys Lys Asn Gly Ala Glu Gln Thr Leu Pro Thr Leu Gly Leu Thr
545                 550                 555                 560

Asn Asn Gln Leu Phe Phe Leu
                565

(2) INFORMATION FOR SEQ ID NO: 20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: genomic DNA
```

(xi) SEQUENCE DESCRIPTION: SEQ ID NO: 20:

GCCAGCGCCG TCTCAAAGTC CAG    23

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 21:

TGGGGGACCT TCAGCAACCT CT    22

(2) INFORMATION FOR SEQ ID NO: 22:

(i) SEQUENCE CHARACTERISTICS:
        (A) LENGTH: 2129 base pairs
        (B) TYPE: nucleic acid
        (C) STRANDEDNESS: single
        (D) TOPOLOGY: linear (ii) MOLECULE TYPE: cDNA for mRNA (xi) SEQUENCE DESCRIPTION: SEQ ID NO: 22:

```
GG ACC CCG GTG GAG AAG CGG CTG GTG GTG CTG GTG GCG CTC CTG GCG      47
   Thr Pro Val Glu Lys Arg Leu Val Val Leu Val Ala Leu Leu Ala
    1               5                  10                  15

GCG GCA TTG GTG GCC TGT TTG GCA GTA CTG GGC ATC CAA TAC CAG ACA     95
Ala Ala Leu Val Ala Cys Leu Ala Val Leu Gly Ile Gln Tyr Gln Thr
                20                  25                  30

AGA ACG CCC TCG GTG TGC CTA AGT GAG GCC TGC ATC TCG GTG ACC AGC    143
Arg Thr Pro Ser Val Cys Leu Ser Glu Ala Cys Ile Ser Val Thr Ser
            35                  40                  45

TCC ATC TTG AGT TCC ATG GAC CCC ACG GTG GAC CCC TGC CAG GAC TTC    191
Ser Ile Leu Ser Ser Met Asp Pro Thr Val Asp Pro Cys Gln Asp Phe
        50                  55                  60

TTC ACC TAT GCC TGT GGC GGC TGG ATC AAA GCC AAC CCC GTG CCG GAT    239
Phe Thr Tyr Ala Cys Gly Gly Trp Ile Lys Ala Asn Pro Val Pro Asp
    65                  70                  75

GGC CAC TCG CGC TGG GGG ACC TTC AGC AAC CTC TGG GAA CAC AAC CAA    287
Gly His Ser Arg Trp Gly Thr Phe Ser Asn Leu Trp Glu His Asn Gln
 80                  85                  90                  95

GCC ATC ATC AAG CAC CTC CTT GAA AAC TCC ACG GCC AGC GTG AGC GAG    335
Ala Ile Ile Lys His Leu Leu Glu Asn Ser Thr Ala Ser Val Ser Glu
                100                 105                 110

GCA GAG AGG AAG GAC CAG GAG TAC TAC CGA GCC TGC ATG AAC GAA ACC    383
Ala Glu Arg Lys Asp Gln Glu Tyr Tyr Arg Ala Cys Met Asn Glu Thr
            115                 120                 125

AGG ATT GAG GAG CTC AAG GCC AAA CCC CTG ATG GAG CTC ATT GAG AAG    431
Arg Ile Glu Glu Leu Lys Ala Lys Pro Leu Met Glu Leu Ile Glu Lys
        130                 135                 140

CTC GGC GGC TGG AAC ATC ACG GGG CCC TGG GAC AAG GAC AAC TTC CAG    479
Leu Gly Gly Trp Asn Ile Thr Gly Pro Trp Asp Lys Asp Asn Phe Gln
    145                 150                 155

GAC ACC CTG CAG GTG GTC ACA TCC CAC TAC CAC ACC TCC CCC TTC TTC    527
Asp Thr Leu Gln Val Val Thr Ser His Tyr His Thr Ser Pro Phe Phe
160                 165                 170                 175

TCC GTC TAC GTC AGT GCC GAC TCC AAG AAT TCC AAC AGC AAC GTG ATC    575
Ser Val Tyr Val Ser Ala Asp Ser Lys Asn Ser Asn Ser Asn Val Ile
                180                 185                 190
```

-continued

```
CAA GTG GAC CAG TCT GGC CTG GGC TTA CCC TCA AGA GAT TAT TAC CTG        623
Gln Val Asp Gln Ser Gly Leu Gly Leu Pro Ser Arg Asp Tyr Tyr Leu
            195                 200                 205

AAC AAA ACC GAG AAT GAG AAG GTG CTG ACG GGA TAC CTG AAC TAC ATG        671
Asn Lys Thr Glu Asn Glu Lys Val Leu Thr Gly Tyr Leu Asn Tyr Met
            210                 215                 220

GTC CAG CTG GGG AAG CTG CTG GGA GGA GGG GCC GAG GAC ACC ATC CGG        719
Val Gln Leu Gly Lys Leu Leu Gly Gly Gly Ala Glu Asp Thr Ile Arg
225                 230                 235

CCC CAG ATG CAG CAG ATC CTG GAC TTT GAG ACG GCG CTG GCC AAC ATC        767
Pro Gln Met Gln Gln Ile Leu Asp Phe Glu Thr Ala Leu Ala Asn Ile
240                 245                 250                 255

ACC ATC CCC CAG GAG AAG CGC CGG GAC GAG GAA CTC ATC TAC CAC AAA        815
Thr Ile Pro Gln Glu Lys Arg Arg Asp Glu Glu Leu Ile Tyr His Lys
            260                 265                 270

GTG ACG GCG GCT GAG TTG CAG ACC TTG GCG CCC GCC ATC AAC TGG CTG        863
Val Thr Ala Ala Glu Leu Gln Thr Leu Ala Pro Ala Ile Asn Trp Leu
            275                 280                 285

CCC TTC CTC AAC ACC ATC TTC TAC CCC GTG GAG ATC AAT GAA TCA GAG        911
Pro Phe Leu Asn Thr Ile Phe Tyr Pro Val Glu Ile Asn Glu Ser Glu
            290                 295                 300

CCT ATT GTC ATC TAC GAC AAA GAA TAC CTG AGC AAG GTC TCC ACC CTC        959
Pro Ile Val Ile Tyr Asp Lys Glu Tyr Leu Ser Lys Val Ser Thr Leu
        305                 310                 315

ATC AAC AGC ACA GAC AAA TGC CTG CTG AAC AAC TAC ATG ATC TGG AAC       1007
Ile Asn Ser Thr Asp Lys Cys Leu Leu Asn Asn Tyr Met Ile Trp Asn
320                 325                 330                 335

CTG GTA CGG AAG ACG AGC TCC TTC CTC GAT CAG CGC TTC CAG GAC GCC       1055
Leu Val Arg Lys Thr Ser Ser Phe Leu Asp Gln Arg Phe Gln Asp Ala
                340                 345                 350

GAC GAG AAG TTC ATG GAA GTC ATG TAT GGG ACC AAG AAG ACG TGT CTT       1103
Asp Glu Lys Phe Met Glu Val Met Tyr Gly Thr Lys Lys Thr Cys Leu
            355                 360                 365

CCC CGC TGG AAG TTT TGT GTG AGT GAT ACA GAG AAC ACC TTG GGC TTC       1151
Pro Arg Trp Lys Phe Cys Val Ser Asp Thr Glu Asn Thr Leu Gly Phe
        370                 375                 380

GCC CTG GGC CCC ATG TTC GTC AAA GCG ACC TTC GCT GAG GAC AGC AAG       1199
Ala Leu Gly Pro Met Phe Val Lys Ala Thr Phe Ala Glu Asp Ser Lys
385                 390                 395

AAC ATA GCC AGC GAG ATC ATC CTG GAG ATC AAG AAG GCG TTT GAA GAG       1247
Asn Ile Ala Ser Glu Ile Ile Leu Glu Ile Lys Lys Ala Phe Glu Glu
400                 405                 410                 415

AGC CTG AGC ACC CTG AAG TGG ATG GAT GAA GAT ACT CGG AAA TCG GCC       1295
Ser Leu Ser Thr Leu Lys Trp Met Asp Glu Asp Thr Arg Lys Ser Ala
                420                 425                 430

AAG GAA AAG GCG GAC GCG ATC TAC AAC ATG ATA GGC TAC CCC AAC TTT       1343
Lys Glu Lys Ala Asp Ala Ile Tyr Asn Met Ile Gly Tyr Pro Asn Phe
            435                 440                 445

ATC ATG GAC CCC AAG GAG CTG GAC AAA GTG TTC AAT GAC TAC ACC GCT       1391
Ile Met Asp Pro Lys Glu Leu Asp Lys Val Phe Asn Asp Tyr Thr Ala
        450                 455                 460

GTG CCA GAC CTC TAC TTC GAG AAC GCC ATG CGG TTT TTC AAC TTC TCC       1439
Val Pro Asp Leu Tyr Phe Glu Asn Ala Met Arg Phe Phe Asn Phe Ser
465                 470                 475

TGG AGG GTC ACT GCC GAC CAG CTC CGG AAA GCG CCC AAC AGA GAT CAG       1487
Trp Arg Val Thr Ala Asp Gln Leu Arg Lys Ala Pro Asn Arg Asp Gln
480                 485                 490                 495

TGG AGC ATG ACC CCG CCC ATG GTG AAC GCC TAC TAC TCG CCC ACC AAG       1535
Trp Ser Met Thr Pro Pro Met Val Asn Ala Tyr Tyr Ser Pro Thr Lys
```

```
                    500                 505                 510
AAC GAG ATC GTG TTT CCG GCC GGA ATC CTG CAG GCG CCA TTC TAC ACC     1583
Asn Glu Ile Val Phe Pro Ala Gly Ile Leu Gln Ala Pro Phe Tyr Thr
                515                 520                 525

CGC TCT TCA CCC AAT GCC TTA AAC TTC GGC GGC ATC GGC GTC GTC GTG     1631
Arg Ser Ser Pro Asn Ala Leu Asn Phe Gly Gly Ile Gly Val Val Val
                530                 535                 540

GGC CAC GAG CTG ACT CAT GCT TTT GAT GAT CAA GGC CGA GAG TAC GAC     1679
Gly His Glu Leu Thr His Ala Phe Asp Asp Gln Gly Arg Glu Tyr Asp
                545                 550                 555

AAG GAT GGG AAC CTC CGG CCC TGG TGG AAG AAC TCG TCC GTG GAG GCG     1727
Lys Asp Gly Asn Leu Arg Pro Trp Trp Lys Asn Ser Ser Val Glu Ala
560                 565                 570                 575

TTC AAG CAG CAG ACC GCG TGC ATG GTG GAG CAG TAC GGC AAC TAT AGC     1775
Phe Lys Gln Gln Thr Ala Cys Met Val Glu Gln Tyr Gly Asn Tyr Ser
                580                 585                 590

GTG AAC GGG GAG CCG GTG AAC GGC CGG CAC ACC CTC GGC GAA AAC ATC     1823
Val Asn Gly Glu Pro Val Asn Gly Arg His Thr Leu Gly Glu Asn Ile
                595                 600                 605

GCC GAC AAC GGG GGC CTC AAG GCG GCC TAT CGG GCC TAC CAG AAC TGG     1871
Ala Asp Asn Gly Gly Leu Lys Ala Ala Tyr Arg Ala Tyr Gln Asn Trp
            610                 615                 620

GTC AAG AAG AAT GGG GCT GAG CAG ACA CTG CCC ACC CTG GGT CTC ACC     1919
Val Lys Lys Asn Gly Ala Glu Gln Thr Leu Pro Thr Leu Gly Leu Thr
625                 630                 635

AAC AAC CAG CTC TTC TTC CTG AGT TTT GCA CAG GTC TGG TGT TCC GTC     1967
Asn Asn Gln Leu Phe Phe Leu Ser Phe Ala Gln Val Trp Cys Ser Val
640                 645                 650                 655

CGC ACC CCC GAG AGT TCG CAC GAA GGT CTC ATC ACC GAT CCC CAC AGC     2015
Arg Thr Pro Glu Ser Ser His Glu Gly Leu Ile Thr Asp Pro His Ser
                660                 665                 670

CCC TCC CGC TTC CGG GTC ATC GGC TCC ATC TCC AAC TCC AAG GAG TTC     2063
Pro Ser Arg Phe Arg Val Ile Gly Ser Ile Ser Asn Ser Lys Glu Phe
                675                 680                 685

TCG GAA CAC TTC CAC TGC CCG CCC GGC TCA CCC ATG AAC CCG CAT CAC     2111
Ser Glu His Phe His Cys Pro Pro Gly Ser Pro Met Asn Pro His His
                690                 695                 700

AAG TGT GAA GTC TGG TGA                                             2129
Lys Cys Glu Val Trp
    705
```

(2) INFORMATION FOR SEQ ID NO: 23:

(i) SEQUENCE CHARACTERISTICS:
        (A) LENGTH: 708 amino acids
        (B) TYPE: amino acid
        (D) TOPOLOGY: linear (ii) MOLECULE TYPE: protein (xi) SEQUENCE DESCRIPTION: SEQ ID NO: 23:

```
Thr Pro Val Glu Lys Arg Leu Val Val Leu Val Ala Leu Leu Ala Ala
 1               5                  10                  15

Ala Leu Val Ala Cys Leu Ala Val Leu Gly Ile Gln Tyr Gln Thr Arg
             20                  25                  30

Thr Pro Ser Val Cys Leu Ser Glu Ala Cys Ile Ser Val Thr Ser Ser
         35                  40                  45

Ile Leu Ser Ser Met Asp Pro Thr Val Asp Pro Cys Gln Asp Phe Phe
     50                  55                  60

Thr Tyr Ala Cys Gly Gly Trp Ile Lys Ala Asn Pro Val Pro Asp Gly
```

```
            65                  70                  75                  80
His Ser Arg Trp Gly Thr Phe Ser Asn Leu Trp Glu His Asn Gln Ala
                    85                  90                  95

Ile Ile Lys His Leu Leu Glu Asn Ser Thr Ala Ser Val Ser Glu Ala
            100                 105                 110

Glu Arg Lys Asp Gln Glu Tyr Tyr Arg Ala Cys Met Asn Glu Thr Arg
        115                 120                 125

Ile Glu Glu Leu Lys Ala Lys Pro Leu Met Glu Leu Ile Glu Lys Leu
    130                 135                 140

Gly Gly Trp Asn Ile Thr Gly Pro Trp Asp Lys Asp Asn Phe Gln Asp
145                 150                 155                 160

Thr Leu Gln Val Val Thr Ser His Tyr His Thr Ser Pro Phe Phe Ser
                165                 170                 175

Val Tyr Val Ser Ala Asp Ser Lys Asn Ser Asn Ser Asn Val Ile Gln
            180                 185                 190

Val Asp Gln Ser Gly Leu Gly Leu Pro Ser Arg Asp Tyr Tyr Leu Asn
        195                 200                 205

Lys Thr Glu Asn Glu Lys Val Leu Thr Gly Tyr Leu Asn Tyr Met Val
    210                 215                 220

Gln Leu Gly Lys Leu Leu Gly Gly Ala Glu Asp Thr Ile Arg Pro
225                 230                 235                 240

Gln Met Gln Gln Ile Leu Asp Phe Glu Thr Ala Leu Ala Asn Ile Thr
                245                 250                 255

Ile Pro Gln Glu Lys Arg Arg Asp Glu Glu Leu Ile Tyr His Lys Val
            260                 265                 270

Thr Ala Ala Glu Leu Gln Thr Leu Ala Pro Ala Ile Asn Trp Leu Pro
        275                 280                 285

Phe Leu Asn Thr Ile Phe Tyr Pro Val Glu Ile Asn Glu Ser Glu Pro
    290                 295                 300

Ile Val Ile Tyr Asp Lys Glu Tyr Leu Ser Lys Val Ser Thr Leu Ile
305                 310                 315                 320

Asn Ser Thr Asp Lys Cys Leu Leu Asn Asn Tyr Met Ile Trp Asn Leu
                325                 330                 335

Val Arg Lys Thr Ser Ser Phe Leu Asp Gln Arg Phe Gln Asp Ala Asp
            340                 345                 350

Glu Lys Phe Met Glu Val Met Tyr Gly Thr Lys Lys Thr Cys Leu Pro
        355                 360                 365

Arg Trp Lys Phe Cys Val Ser Asp Thr Glu Asn Thr Leu Gly Phe Ala
    370                 375                 380

Leu Gly Pro Met Phe Val Lys Ala Thr Phe Ala Glu Asp Ser Lys Asn
385                 390                 395                 400

Ile Ala Ser Glu Ile Ile Leu Glu Ile Lys Lys Ala Phe Glu Glu Ser
                405                 410                 415

Leu Ser Thr Leu Lys Trp Met Asp Glu Asp Thr Arg Lys Ser Ala Lys
            420                 425                 430

Glu Lys Ala Asp Ala Ile Tyr Asn Met Ile Gly Tyr Pro Asn Phe Ile
        435                 440                 445

Met Asp Pro Lys Glu Leu Asp Lys Val Phe Asn Asp Tyr Thr Ala Val
    450                 455                 460

Pro Asp Leu Tyr Phe Glu Asn Ala Met Arg Phe Phe Asn Phe Ser Trp
465                 470                 475                 480

Arg Val Thr Ala Asp Gln Leu Arg Lys Ala Pro Asn Arg Asp Gln Trp
                485                 490                 495
```

```
Ser Met Thr Pro Pro Met Val Asn Ala Tyr Tyr Ser Pro Thr Lys Asn
            500                 505                 510

Glu Ile Val Phe Pro Ala Gly Ile Leu Gln Ala Pro Phe Tyr Thr Arg
            515                 520                 525

Ser Ser Pro Asn Ala Leu Asn Phe Gly Gly Ile Gly Val Val Val Gly
            530                 535                 540

His Glu Leu Thr His Ala Phe Asp Asp Gln Gly Arg Glu Tyr Asp Lys
545                 550                 555                 560

Asp Gly Asn Leu Arg Pro Trp Trp Lys Asn Ser Ser Val Glu Ala Phe
                565                 570                 575

Lys Gln Gln Thr Ala Cys Met Val Glu Gln Tyr Gly Asn Tyr Ser Val
            580                 585                 590

Asn Gly Glu Pro Val Asn Gly Arg His Thr Leu Gly Glu Asn Ile Ala
            595                 600                 605

Asp Asn Gly Gly Leu Lys Ala Ala Tyr Arg Ala Tyr Gln Asn Trp Val
610                 615                 620

Lys Lys Asn Gly Ala Glu Gln Thr Leu Pro Thr Leu Gly Leu Thr Asn
625                 630                 635                 640

Asn Gln Leu Phe Phe Leu Ser Phe Ala Gln Val Trp Cys Ser Val Arg
                645                 650                 655

Thr Pro Glu Ser Ser His Glu Gly Leu Ile Thr Asp Pro His Ser Pro
            660                 665                 670

Ser Arg Phe Arg Val Ile Gly Ser Ile Ser Asn Ser Lys Glu Phe Ser
            675                 680                 685

Glu His Phe His Cys Pro Pro Gly Ser Pro Met Asn Pro His His Lys
            690                 695                 700

Cys Glu Val Trp
705

(2) INFORMATION FOR SEQ ID NO: 24:

(i) SEQUENCE CHARACTERISTICS:
        (A) LENGTH: 2533 base pairs
        (B) TYPE: nucleic acid
        (C) STRANDEDNESS: single
        (D) TOPOLOGY: linear (ii) MOLECULE TYPE: cDNA for mRNA (xi) SEQUENCE DESCRIPTION: SEQ ID NO: 24:

CGG CTG GTG GTG TTG GTG GTA CTT CTG GCG GCA GGA CTG GTG GCC TGC      48
Arg Leu Val Val Leu Val Val Leu Leu Ala Ala Gly Leu Val Ala Cys
  1               5                  10                  15

TTG GCA GCA CTG GGC ATC CAG TAC CAG ACA AGA TCC CCC TCT GTG TGC      96
Leu Ala Ala Leu Gly Ile Gln Tyr Gln Thr Arg Ser Pro Ser Val Cys
                 20                  25                  30

CTG AGC GAA GCT TGT GTC TCA GTG ACC AGC TCC ATC TTG AGC TCC ATG     144
Leu Ser Glu Ala Cys Val Ser Val Thr Ser Ser Ile Leu Ser Ser Met
             35                  40                  45

GAC CCC ACA GTG GAC CCC TGC CAT GAC TTC TTC AGC TAC GCC TGT GGG     192
Asp Pro Thr Val Asp Pro Cys His Asp Phe Phe Ser Tyr Ala Cys Gly
         50                  55                  60

GGC TGG ATC AAG GCC AAC CCA GTC CCT GAT GGC CAC TCA CGC TGG GGG     240
Gly Trp Ile Lys Ala Asn Pro Val Pro Asp Gly His Ser Arg Trp Gly
 65                  70                  75                  80

ACC TTC AGC AAC CTC TGG GAA CAC AAC CAA GCA ATC ATC AAG CAC CTC     288
Thr Phe Ser Asn Leu Trp Glu His Asn Gln Ala Ile Ile Lys His Leu
                 85                  90                  95
```

```
CTC GAA AAC TCC ACG GCC AGC GTG AGC GAG GCA GAG AGA AAG GCG CAA      336
Leu Glu Asn Ser Thr Ala Ser Val Ser Glu Ala Glu Arg Lys Ala Gln
            100                 105                 110

GTA TAC TAC CGT GCG TGC ATG AAC GAG ACC AGG ATC GAG GAG CTC AGG      384
Val Tyr Tyr Arg Ala Cys Met Asn Glu Thr Arg Ile Glu Glu Leu Arg
                115                 120                 125

GCC AAA CCT CTA ATG GAG TTG ATT GAG AGG CTC GGG GGC TGG AAC ATC      432
Ala Lys Pro Leu Met Glu Leu Ile Glu Arg Leu Gly Gly Trp Asn Ile
        130                 135                 140

ACA GGT CCC TGG GCC AAG GAC AAC TTC CAG GAC ACC CTG CAG GTG GTC      480
Thr Gly Pro Trp Ala Lys Asp Asn Phe Gln Asp Thr Leu Gln Val Val
145                 150                 155                 160

ACC GCC CAC TAC CGC ACC TCA CCC TTC TTC TCT GTC TAT GTC AGT GCC      528
Thr Ala His Tyr Arg Thr Ser Pro Phe Phe Ser Val Tyr Val Ser Ala
                165                 170                 175

GAT TCC AAG AAC TCC AAC AGC AAC GTG ATC CAG GTG GAC CAG TCT GGC      576
Asp Ser Lys Asn Ser Asn Ser Asn Val Ile Gln Val Asp Gln Ser Gly
                180                 185                 190

CTG GGC TTG CCC TCG AGA GAC TAT TAC CTG AAC AAA ACT GAA AAC GAG      624
Leu Gly Leu Pro Ser Arg Asp Tyr Tyr Leu Asn Lys Thr Glu Asn Glu
                195                 200                 205

AAG GTG CTG ACC GGA TAT CTG AAC TAC ATG GTC CAG CTG GGG AAG CTG      672
Lys Val Leu Thr Gly Tyr Leu Asn Tyr Met Val Gln Leu Gly Lys Leu
        210                 215                 220

CTG GGC GGC GGG GAC GAG GAG GCC ATC CGG CCC CAG ATG CAG CAG ATC      720
Leu Gly Gly Gly Asp Glu Glu Ala Ile Arg Pro Gln Met Gln Gln Ile
225                 230                 235                 240

TTG GAC TTT GAG ACG GCA CTG GCC AAC ATC ACC ATC CCA CAG GAG AAG      768
Leu Asp Phe Glu Thr Ala Leu Ala Asn Ile Thr Ile Pro Gln Glu Lys
                245                 250                 255

CGC CGT GAT GAG GAG CTC ATC TAC CAC AAA GTG ACG GCA GCC GAG CTG      816
Arg Arg Asp Glu Glu Leu Ile Tyr His Lys Val Thr Ala Ala Glu Leu
                260                 265                 270

CAG ACC TTG GCA CCC GCC ATC AAC TGG TTG CCT TTT CTC AAC ACC ATC      864
Gln Thr Leu Ala Pro Ala Ile Asn Trp Leu Pro Phe Leu Asn Thr Ile
        275                 280                 285

TTC TAC CCC GTG GAG ATC AAT GAA TCC GAG CCT ATT GTG GTC TAT GAC      912
Phe Tyr Pro Val Glu Ile Asn Glu Ser Glu Pro Ile Val Val Tyr Asp
        290                 295                 300

AAG GAA TAC CTT GAG CAG ATC TCC ACT CTC ATC AAC ACC ACC GAC AGA      960
Lys Glu Tyr Leu Glu Gln Ile Ser Thr Leu Ile Asn Thr Thr Asp Arg
305                 310                 315                 320

TGC CTG CTC AAC AAC TAC ATG ATC TGG AAC CTG GTG CGG AAA ACA AGC     1008
Cys Leu Leu Asn Asn Tyr Met Ile Trp Asn Leu Val Arg Lys Thr Ser
                325                 330                 335

TCC TTC CTT GAC CAG CGC TTT CAG GAC GCC GAT GAG AAG TTC ATG GAA     1056
Ser Phe Leu Asp Gln Arg Phe Gln Asp Ala Asp Glu Lys Phe Met Glu
        340                 345                 350

GTC ATG TAC GGG ACC AAG AAG ACC TGT CTT CCT CGC TGG AAG TTT TGC     1104
Val Met Tyr Gly Thr Lys Lys Thr Cys Leu Pro Arg Trp Lys Phe Cys
                355                 360                 365

GTG AGT GAC ACA GAA AAC AAC CTG GGC TTT GCG TTG GGC CCC ATG TTT     1152
Val Ser Asp Thr Glu Asn Asn Leu Gly Phe Ala Leu Gly Pro Met Phe
        370                 375                 380

GTC AAA GCA ACC TTC GCC GAG GAC AGC AAG AGC ATA GCC ACC GAG ATC     1200
Val Lys Ala Thr Phe Ala Glu Asp Ser Lys Ser Ile Ala Thr Glu Ile
385                 390                 395                 400

ATC CTG GAG ATT AAG AAG GCA TTT GAG GAA AGC CTG AGC ACC CTG AAG     1248
Ile Leu Glu Ile Lys Lys Ala Phe Glu Glu Ser Leu Ser Thr Leu Lys
```

```
                405                  410                   415
TGG ATG GAT GAG GAA ACC CGA AAA TCA GCC AAG GAA AAG GCC GAT GCC   1296
Trp Met Asp Glu Glu Thr Arg Lys Ser Ala Lys Glu Lys Ala Asp Ala
            420                 425                 430

ATC TAC AAC ATG ATA GGA TAC CCC AAC TTC ATC ATG GAT CCC AAG GAG   1344
Ile Tyr Asn Met Ile Gly Tyr Pro Asn Phe Ile Met Asp Pro Lys Glu
            435                 440                 445

CTG GAC AAA GTG TTT AAT GAC TAC ACT GCA GTT CCA GAC CTC TAC TTT   1392
Leu Asp Lys Val Phe Asn Asp Tyr Thr Ala Val Pro Asp Leu Tyr Phe
450                 455                 460

GAA AAT GCC ATG CGG TTT TTC AAC TTC TCA TGG AGG GTC ACT GCC GAT   1440
Glu Asn Ala Met Arg Phe Phe Asn Phe Ser Trp Arg Val Thr Ala Asp
465                 470                 475                 480

CAG CTC AGG AAA GCC CCC AAC AGA GAT CAG TGG AGC ATG ACC CCG CCC   1488
Gln Leu Arg Lys Ala Pro Asn Arg Asp Gln Trp Ser Met Thr Pro Pro
                485                 490                 495

ATG GTG AAC GCC TAC TAC TCG CCC ACC AAG AAT GAG ATT GTG TTT CCG   1536
Met Val Asn Ala Tyr Tyr Ser Pro Thr Lys Asn Glu Ile Val Phe Pro
            500                 505                 510

GCC GGG ATC CTG CAG GCA CCA TTC TAC ACA CGC TCC TCA CCC AAG GCC   1584
Ala Gly Ile Leu Gln Ala Pro Phe Tyr Thr Arg Ser Ser Pro Lys Ala
            515                 520                 525

TTA AAC TTT GGT GGC ATA GGT GTC GTC GTG GGC CAT GAG CTG ACT CAT   1632
Leu Asn Phe Gly Gly Ile Gly Val Val Val Gly His Glu Leu Thr His
            530                 535                 540

GCT TTT GAT GAT CAA GGA CGG GAG TAT GAC AAG GAC GGG AAC CTC CGG   1680
Ala Phe Asp Asp Gln Gly Arg Glu Tyr Asp Lys Asp Gly Asn Leu Arg
545                 550                 555                 560

CCA TGG TGG AAG AAC TCA TCC GTG GAG GCC TTC AAG CGT CAG ACC GAG   1728
Pro Trp Trp Lys Asn Ser Ser Val Glu Ala Phe Lys Arg Gln Thr Glu
                565                 570                 575

TGC ATG GTA GAG CAG TAC AGC AAC TAC AGC GTG AAC GGG GAG CCG GTG   1776
Cys Met Val Glu Gln Tyr Ser Asn Tyr Ser Val Asn Gly Glu Pro Val
            580                 585                 590

AAC GGG CGG CAC ACC CTG GGG GAG AAC ATC GCC GAC AAC GGG GGT CTC   1824
Asn Gly Arg His Thr Leu Gly Glu Asn Ile Ala Asp Asn Gly Gly Leu
            595                 600                 605

AAG GCG GCC TAT CGG GCT TAC CAG AAC TGG GTG AAG AAG AAC GGG GCT   1872
Lys Ala Ala Tyr Arg Ala Tyr Gln Asn Trp Val Lys Lys Asn Gly Ala
610                 615                 620

GAG CAC TCG CTC CCC ACC CTG GGC CTC ACC AAT AAC CAG CTC TTC TTC   1920
Glu His Ser Leu Pro Thr Leu Gly Leu Thr Asn Asn Gln Leu Phe Phe
625                 630                 635                 640

CTG GGC TTT GCA CAG GTC TGG TGC TCC GTC CGC ACA CCT GAG AGC TCC   1968
Leu Gly Phe Ala Gln Val Trp Cys Ser Val Arg Thr Pro Glu Ser Ser
                645                 650                 655

CAC GAA GGC CTC ATC ACC GAT CCC CAC AGC CCC TCT CGC TTC CGG GTC   2016
His Glu Gly Leu Ile Thr Asp Pro His Ser Pro Ser Arg Phe Arg Val
            660                 665                 670

ATC GGC TCC CTC TCC AAT TCC AAG GAG TTC TCA GAA CAC TTC CGC TGC   2064
Ile Gly Ser Leu Ser Asn Ser Lys Glu Phe Ser Glu His Phe Arg Cys
            675                 680                 685

CCA CCT GGC TCA CCC ATG AAC CCG CCT CAC AAG TGC GAA GTC TGG       2109
Pro Pro Gly Ser Pro Met Asn Pro Pro His Lys Cys Glu Val Trp
            690                 695                 700

TAAGGACGAA GCGGAGAGAG CCAAGACGGA GGAGGGGAAG GGGCTGAGGA CGAGACCCCC   2169

ATCCAGCCTC CAGGGCATTG CTCAGCCCGC TTGGCCACCC GGGGCCCTGC TTCCTCACAC   2229

TGGCGGGTTT TCAGCCGGAA CCGAGCCCAT GGTGTTGGCT CTCAACGTGA CCCGCAGTCT   2289
```

-continued

```
GATCCCCTGT GAAGAGCCGG ACATCCCAGG CACACGTGTG CGCCACCTTC AGCAGGCATT      2349

CGGGTGCTGG GCTGGTGGCT CATCAGGCCT GGGCCCCACA CTGACAAGCG CCAGATACGC      2409

CACAAATACC ACTGTGTCAA ATGCTTTCAA GATATATTTT TGGGGAAACT ATTTTTTAAA      2469

CACTGTGGAA TACACTGGAA ATCTTCAGGG AAAAACACAT TTAAACACTT TTTTTTTTAA      2529

GCCC                                                                    2533
```

(2) INFORMATION FOR SEQ ID NO: 25:

(i) SEQUENCE CHARACTERISTICS:
        (A) LENGTH: 703 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 25:

```
Arg Leu Val Val Leu Val Val Leu Leu Ala Ala Gly Leu Val Ala Cys
 1               5                  10                  15

Leu Ala Ala Leu Gly Ile Gln Tyr Gln Thr Arg Ser Pro Ser Val Cys
            20                  25                  30

Leu Ser Glu Ala Cys Val Ser Val Thr Ser Ser Ile Leu Ser Ser Met
        35                  40                  45

Asp Pro Thr Val Asp Pro Cys His Asp Phe Phe Ser Tyr Ala Cys Gly
    50                  55                  60

Gly Trp Ile Lys Ala Asn Pro Val Pro Asp Gly His Ser Arg Trp Gly
65                  70                  75                  80

Thr Phe Ser Asn Leu Trp Glu His Asn Gln Ala Ile Ile Lys His Leu
                85                  90                  95

Leu Glu Asn Ser Thr Ala Ser Val Ser Glu Ala Glu Arg Lys Ala Gln
            100                 105                 110

Val Tyr Tyr Arg Ala Cys Met Asn Glu Thr Arg Ile Glu Glu Leu Arg
        115                 120                 125

Ala Lys Pro Leu Met Glu Leu Ile Glu Arg Leu Gly Gly Trp Asn Ile
    130                 135                 140

Thr Gly Pro Trp Ala Lys Asp Asn Phe Gln Asp Thr Leu Gln Val Val
145                 150                 155                 160

Thr Ala His Tyr Arg Thr Ser Pro Phe Phe Ser Val Tyr Val Ser Ala
                165                 170                 175

Asp Ser Lys Asn Ser Asn Ser Asn Val Ile Gln Val Asp Gln Ser Gly
            180                 185                 190

Leu Gly Leu Pro Ser Arg Asp Tyr Tyr Leu Asn Lys Thr Glu Asn Glu
        195                 200                 205

Lys Val Leu Thr Gly Tyr Leu Asn Tyr Met Val Gln Leu Gly Lys Leu
    210                 215                 220

Leu Gly Gly Gly Asp Glu Glu Ala Ile Arg Pro Gln Met Gln Gln Ile
225                 230                 235                 240

Leu Asp Phe Glu Thr Ala Leu Ala Asn Ile Thr Ile Pro Gln Glu Lys
                245                 250                 255

Arg Arg Asp Glu Glu Leu Ile Tyr His Lys Val Thr Ala Ala Glu Leu
            260                 265                 270

Gln Thr Leu Ala Pro Ala Ile Asn Trp Leu Pro Phe Leu Asn Thr Ile
        275                 280                 285

Phe Tyr Pro Val Glu Ile Asn Glu Ser Glu Pro Ile Val Val Tyr Asp
```

```
            290                 295                 300
Lys Glu Tyr Leu Glu Gln Ile Ser Thr Leu Ile Asn Thr Thr Asp Arg
305                 310                 315                 320
Cys Leu Asn Asn Tyr Met Ile Trp Asn Leu Val Arg Lys Thr Ser
                325                 330                 335
Ser Phe Leu Asp Gln Arg Phe Gln Asp Ala Asp Glu Lys Phe Met Glu
            340                 345                 350
Val Met Tyr Gly Thr Lys Lys Thr Cys Leu Pro Arg Trp Lys Phe Cys
            355                 360                 365
Val Ser Asp Thr Glu Asn Asn Leu Gly Phe Ala Leu Gly Pro Met Phe
        370                 375                 380
Val Lys Ala Thr Phe Ala Glu Asp Ser Lys Ser Ile Ala Thr Glu Ile
385                 390                 395                 400
Ile Leu Glu Ile Lys Lys Ala Phe Glu Glu Ser Leu Ser Thr Leu Lys
                405                 410                 415
Trp Met Asp Glu Glu Thr Arg Lys Ser Ala Lys Glu Lys Ala Asp Ala
            420                 425                 430
Ile Tyr Asn Met Ile Gly Tyr Pro Asn Phe Ile Met Asp Pro Lys Glu
                435                 440                 445
Leu Asp Lys Val Phe Asn Asp Tyr Thr Ala Val Pro Asp Leu Tyr Phe
450                 455                 460
Glu Asn Ala Met Arg Phe Phe Asn Phe Ser Trp Arg Val Thr Ala Asp
465                 470                 475                 480
Gln Leu Arg Lys Ala Pro Asn Arg Asp Gln Trp Ser Met Thr Pro Pro
                485                 490                 495
Met Val Asn Ala Tyr Tyr Ser Pro Thr Lys Asn Glu Ile Val Phe Pro
                500                 505                 510
Ala Gly Ile Leu Gln Ala Pro Phe Tyr Thr Arg Ser Ser Pro Lys Ala
            515                 520                 525
Leu Asn Phe Gly Gly Ile Gly Val Val Gly His Glu Leu Thr His
            530                 535                 540
Ala Phe Asp Asp Gln Gly Arg Glu Tyr Asp Lys Asp Gly Asn Leu Arg
545                 550                 555                 560
Pro Trp Trp Lys Asn Ser Ser Val Glu Ala Phe Lys Arg Gln Thr Glu
                565                 570                 575
Cys Met Val Glu Gln Tyr Ser Asn Tyr Ser Val Asn Gly Glu Pro Val
                580                 585                 590
Asn Gly Arg His Thr Leu Gly Glu Asn Ile Ala Asp Asn Gly Gly Leu
            595                 600                 605
Lys Ala Ala Tyr Arg Ala Tyr Gln Asn Trp Val Lys Lys Asn Gly Ala
            610                 615                 620
Glu His Ser Leu Pro Thr Leu Gly Leu Thr Asn Asn Gln Leu Phe Phe
625                 630                 635                 640
Leu Gly Phe Ala Gln Val Trp Cys Ser Val Arg Thr Pro Glu Ser Ser
                645                 650                 655
His Glu Gly Leu Ile Thr Asp Pro His Ser Pro Ser Arg Phe Arg Val
                660                 665                 670
Ile Gly Ser Leu Ser Asn Ser Lys Glu Phe Ser Glu His Phe Arg Cys
                675                 680                 685
Pro Pro Gly Ser Pro Met Asn Pro Pro His Lys Cys Glu Val Trp
            690                 695                 700

(2) INFORMATION FOR SEQ ID NO: 26:
```

```
        (i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: genomic DNA (xi) SEQUENCE DESCRIPTION: SEQ ID NO: 26:

GGTGCTTGAT GATGGCTTGG TTGT                                                24

(2) INFORMATION FOR SEQ ID NO: 27:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: genomic DNA (xi) SEQUENCE DESCRIPTION: SEQ ID NO: 27:

AGATGGAGCT GGTCACCGAG ATGC                                                24

(2) INFORMATION FOR SEQ ID NO: 28:

(i) SEQUENCE CHARACTERISTICS:
            (A) LENGTH: 324 base pairs
            (B) TYPE: nucleic acid
            (C) STRANDEDNESS: single
            (D) TOPOLOGY: linear (ii) MOLECULE TYPE: cDNA for mRNA (xi) SEQUENCE DESCRIPTION: SEQ ID NO: 28:

GGGAGCGCGG CGCGGGGCCG GAGCGGAGCG CGCGAGCGAT GATGTCTACC TACAAGCGGC          60

CCACGCTGGA CGAGGAGGAC CTGGTGGACT CGCTGTCCGA GAGCGACGTG TACCCCAACC         120

ACCTGCAGGT GAACTTCCGA GGCCCCCGGA ACGGCCAGAG ATGCTGGGCC GCCAGGACCC         180

CGGTGGAGAA GCGGCTGGTG GTGCTGGTGG CGCTCCTGGC GGCGGCATTG GTGGCCTGTT         240

TGGCAGTACT GGGCATCCAA TACCAGACAA GAACGCCCTC GGTGTGCCTA AGTGAGGCCT         300

GCATCTCGGT GACCAGCTCC ATCT                                               324

(2) INFORMATION FOR SEQ ID NO: 29:

(i) SEQUENCE CHARACTERISTICS:
            (A) LENGTH: 2314 base pairs
            (B) TYPE: nucleic acid
            (C) STRANDEDNESS: single
            (D) TOPOLOGY: linear (ii) MOLECULE TYPE: cDNA for mRNA (xi) SEQUENCE DESCRIPTION: SEQ ID NO: 29:

GGGAGCGCGG CGCGGGGCCG GAGCGGAGCG CGCGAGCG ATG ATG TCT ACC TAC             53
                                         Met Met Ser Thr Tyr
                                           1               5

AAG CGG CCC ACG CTG GAC GAG GAG GAC CTG GTG GAC TCG CTG TCC GAG          101
Lys Arg Pro Thr Leu Asp Glu Glu Asp Leu Val Asp Ser Leu Ser Glu
             10                  15                  20

AGC GAC GTG TAC CCC AAC CAC CTG CAG GTG AAC TTC CGA GGC CCC CGG          149
Ser Asp Val Tyr Pro Asn His Leu Gln Val Asn Phe Arg Gly Pro Arg
         25                  30                  35

AAC GGC CAG AGA TGC TGG GCC GCC AGG ACC CCG GTG GAG AAG CGG CTG          197
```

```
                Asn Gly Gln Arg Cys Trp Ala Ala Arg Thr Pro Val Glu Lys Arg Leu
                         40                  45                  50

GTG GTG CTG GTG GCG CTC CTG GCG GCG GCA TTG GTG GCC TGT TTG GCA              245
Val Val Leu Val Ala Leu Leu Ala Ala Ala Leu Val Ala Cys Leu Ala
         55                  60                  65

GTA CTG GGC ATC CAA TAC CAG ACA AGA ACG CCC TCG GTG TGC CTA AGT              293
Val Leu Gly Ile Gln Tyr Gln Thr Arg Thr Pro Ser Val Cys Leu Ser
70                   75                  80                  85

GAG GCC TGC ATC TCG GTG ACC AGC TCC ATC TTG AGT TCC ATG GAC CCC              341
Glu Ala Cys Ile Ser Val Thr Ser Ser Ile Leu Ser Ser Met Asp Pro
                 90                  95                 100

ACG GTG GAC CCC TGC CAG GAC TTC TTC ACC TAT GCC TGT GGC GGC TGG              389
Thr Val Asp Pro Cys Gln Asp Phe Phe Thr Tyr Ala Cys Gly Gly Trp
             105                 110                 115

ATC AAA GCC AAC CCC GTG CCG GAT GGC CAC TCG CGC TGG GGG ACC TTC              437
Ile Lys Ala Asn Pro Val Pro Asp Gly His Ser Arg Trp Gly Thr Phe
         120                 125                 130

AGC AAC CTC TGG GAA CAC AAC CAA GCC ATC ATC AAG CAC CTC CTT GAA              485
Ser Asn Leu Trp Glu His Asn Gln Ala Ile Ile Lys His Leu Leu Glu
     135                 140                 145

AAC TCC ACG GCC AGC GTG AGC GAG GCA GAG AGG AAG GAC CAG GAG TAC              533
Asn Ser Thr Ala Ser Val Ser Glu Ala Glu Arg Lys Asp Gln Glu Tyr
150                 155                 160                 165

TAC CGA GCC TGC ATG AAC GAA ACC AGG ATT GAG GAG CTC AAG GCC AAA              581
Tyr Arg Ala Cys Met Asn Glu Thr Arg Ile Glu Glu Leu Lys Ala Lys
                 170                 175                 180

CCC CTG ATG GAG CTC ATT GAG AAG CTC GGC GGC TGG AAC ATC ACG GGG              629
Pro Leu Met Glu Leu Ile Glu Lys Leu Gly Gly Trp Asn Ile Thr Gly
             185                 190                 195

CCC TGG GAC AAG GAC AAC TTC CAG GAC ACC CTG CAG GTG GTC ACA TCC              677
Pro Trp Asp Lys Asp Asn Phe Gln Asp Thr Leu Gln Val Val Thr Ser
         200                 205                 210

CAC TAC CAC ACC TCC CCC TTC TTC TCC GTC TAC GTC AGT GCC GAC TCC              725
His Tyr His Thr Ser Pro Phe Phe Ser Val Tyr Val Ser Ala Asp Ser
     215                 220                 225

AAG AAT TCC AAC AGC AAC GTG ATC CAA GTG GAC CAG TCT GGC CTG GGC              773
Lys Asn Ser Asn Ser Asn Val Ile Gln Val Asp Gln Ser Gly Leu Gly
230                 235                 240                 245

TTA CCC TCA AGA GAT TAT TAC CTG AAC AAA ACC GAG AAT GAG AAG GTG              821
Leu Pro Ser Arg Asp Tyr Tyr Leu Asn Lys Thr Glu Asn Glu Lys Val
                 250                 255                 260

CTG ACG GGA TAC CTG AAC TAC ATG GTC CAG CTG GGG AAG CTG CTG GGA              869
Leu Thr Gly Tyr Leu Asn Tyr Met Val Gln Leu Gly Lys Leu Leu Gly
             265                 270                 275

GGA GGG GCC GAG GAC ACC ATC CGG CCC CAG ATG CAG CAG ATC CTG GAC              917
Gly Gly Ala Glu Asp Thr Ile Arg Pro Gln Met Gln Gln Ile Leu Asp
         280                 285                 290

TTT GAG ACG GCG CTG GCC AAC ATC ACC ATC CCC CAG GAG AAG CGC CGG              965
Phe Glu Thr Ala Leu Ala Asn Ile Thr Ile Pro Gln Glu Lys Arg Arg
     295                 300                 305

GAC GAG GAA CTC ATC TAC CAC AAA GTG ACG GCG GCT GAG TTG CAG ACC             1013
Asp Glu Glu Leu Ile Tyr His Lys Val Thr Ala Ala Glu Leu Gln Thr
310                 315                 320                 325

TTG GCG CCC GCC ATC AAC TGG CTG CCC TTC CTC AAC ACC ATC TTC TAC             1061
Leu Ala Pro Ala Ile Asn Trp Leu Pro Phe Leu Asn Thr Ile Phe Tyr
                 330                 335                 340

CCC GTG GAG ATC AAT GAA TCA GAG CCT ATT GTC ATC TAC GAC AAA GAA             1109
Pro Val Glu Ile Asn Glu Ser Glu Pro Ile Val Ile Tyr Asp Lys Glu
             345                 350                 355
```

```
TAC CTG AGC AAG GTC TCC ACC CTC ATC AAC AGC ACA GAC AAA TGC CTG      1157
Tyr Leu Ser Lys Val Ser Thr Leu Ile Asn Ser Thr Asp Lys Lys Leu
            360                 365                 370

CTG AAC AAC TAC ATG ATC TGG AAC CTG GTA CGG AAG ACG AGC TCC TTC      1205
Leu Asn Asn Tyr Met Ile Trp Asn Leu Val Arg Lys Thr Ser Ser Phe
        375                 380                 385

CTC GAT CAG CGC TTC CAG GAC GCC GAC GAG AAG TTC ATG GAA GTC ATG      1253
Leu Asp Gln Arg Phe Gln Asp Ala Asp Glu Lys Phe Met Glu Val Met
390                 395                 400                 405

TAT GGG ACC AAG AAG ACG TGT CTT CCC CGC TGG AAG TTT TGT GTG AGT      1301
Tyr Gly Thr Lys Lys Thr Cys Leu Pro Arg Trp Lys Phe Cys Val Ser
                410                 415                 420

GAT ACA GAG AAC ACC TTG GGC TTC GCC CTG GGC CCC ATG TTC GTC AAA      1349
Asp Thr Glu Asn Thr Leu Gly Phe Ala Leu Gly Pro Met Phe Val Lys
            425                 430                 435

GCG ACC TTC GCT GAG GAC AGC AAG AAC ATA GCC AGC GAG ATC ATC CTG      1397
Ala Thr Phe Ala Glu Asp Ser Lys Asn Ile Ala Ser Glu Ile Ile Leu
        440                 445                 450

GAG ATC AAG AAG GCG TTT GAA GAG AGC CTG AGC ACC CTG AAG TGG ATG      1445
Glu Ile Lys Lys Ala Phe Glu Glu Ser Leu Ser Thr Leu Lys Trp Met
455                 460                 465

GAT GAA GAT ACT CGG AAA TCG GCC AAG GAA AAG GCG GAC GCG ATC TAC      1493
Asp Glu Asp Thr Arg Lys Ser Ala Lys Glu Lys Ala Asp Ala Ile Tyr
470                 475                 480                 485

AAC ATG ATA GGC TAC CCC AAC TTT ATC ATG GAC CCC AAG GAG CTG GAC      1541
Asn Met Ile Gly Tyr Pro Asn Phe Ile Met Asp Pro Lys Glu Leu Asp
                490                 495                 500

AAA GTG TTC AAT GAC TAC ACC GCT GTG CCA GAC CTC TAC TTC GAG AAC      1589
Lys Val Phe Asn Asp Tyr Thr Ala Val Pro Asp Leu Tyr Phe Glu Asn
            505                 510                 515

GCC ATG CGG TTT TTC AAC TTC TCC TGG AGG GTC ACT GCC GAC CAG CTC      1637
Ala Met Arg Phe Phe Asn Phe Ser Trp Arg Val Thr Ala Asp Gln Leu
        520                 525                 530

CGG AAA GCG CCC AAC AGA GAT CAG TGG AGC ATG ACC CCG CCC ATG GTG      1685
Arg Lys Ala Pro Asn Arg Asp Gln Trp Ser Met Thr Pro Pro Met Val
535                 540                 545

AAC GCC TAC TAC TCG CCC ACC AAG AAC GAG ATC GTG TTT CCG GCC GGA      1733
Asn Ala Tyr Tyr Ser Pro Thr Lys Asn Glu Ile Val Phe Pro Ala Gly
550                 555                 560                 565

ATC CTG CAG GCG CCA TTC TAC ACC CGC TCT TCA CCC AAT GCC TTA AAC      1781
Ile Leu Gln Ala Pro Phe Tyr Thr Arg Ser Ser Pro Asn Ala Leu Asn
                570                 575                 580

TTC GGC GGC ATC GGC GTC GTC GTG GGC CAC GAG CTG ACT CAT GCT TTT      1829
Phe Gly Gly Ile Gly Val Val Val Gly His Glu Leu Thr His Ala Phe
            585                 590                 595

GAT GAT CAA GGC CGA GAG TAC GAC AAG GAT GGG AAC CTC CGG CCC TGG      1877
Asp Asp Gln Gly Arg Glu Tyr Asp Lys Asp Gly Asn Leu Arg Pro Trp
        600                 605                 610

TGG AAG AAC TCG TCC GTG GAG GCG TTC AAG CAG CAG ACC GCG TGC ATG      1925
Trp Lys Asn Ser Ser Val Glu Ala Phe Lys Gln Gln Thr Ala Cys Met
615                 620                 625

GTG GAG CAG TAC GGC AAC TAT AGC GTG AAC GGG GAG CCG GTG AAC GGC      1973
Val Glu Gln Tyr Gly Asn Tyr Ser Val Asn Gly Glu Pro Val Asn Gly
630                 635                 640                 645

CGG CAC ACC CTC GGC GAA AAC ATC GCC GAC AAC GGG GGC CTC AAG GCG      2021
Arg His Thr Leu Gly Glu Asn Ile Ala Asp Asn Gly Gly Leu Lys Ala
                650                 655                 660

GCC TAT CGG GCC TAC CAG AAC TGG GTC AAG AAG AAT GGG GCT GAG CAG      2069
Ala Tyr Arg Ala Tyr Gln Asn Trp Val Lys Lys Asn Gly Ala Glu Gln
            665                 670                 675
```

```
ACA CTG CCC ACC CTG GGT CTC ACC AAC AAC CAG CTC TTC TTC CTG AGT    2117
Thr Leu Pro Thr Leu Gly Leu Thr Asn Asn Gln Leu Phe Phe Leu Ser
            680                 685                 690

TTT GCA CAG GTC TGG TGT TCC GTC CGC ACC CCC GAG AGT TCG CAC GAA    2165
Phe Ala Gln Val Trp Cys Ser Val Arg Thr Pro Glu Ser Ser His Glu
    695                 700                 705

GGT CTC ATC ACC GAT CCC CAC AGC CCC TCC CGC TTC CGG GTC ATC GGC    2213
Gly Leu Ile Thr Asp Pro His Ser Pro Ser Arg Phe Arg Val Ile Gly
710             715                 720                 725

TCC ATC TCC AAC TCC AAG GAG TTC TCG GAA CAC TTC CAC TGC CCG CCC    2261
Ser Ile Ser Asn Ser Lys Glu Phe Ser Glu His Phe His Cys Pro Pro
                730                 735                 740

GGC TCA CCC ATG AAC CCG CAT CAC AAG TGT GAA GTC TGG T GAAGGGCCAG   2311
Gly Ser Pro Met Asn Pro His His Lys Cys Glu Val Trp
                745                 750

GCA                                                                2314
```

(2) INFORMATION FOR SEQ ID NO: 30:

(i) SEQUENCE CHARACTERISTICS:
        (A) LENGTH: 754 amino acids
        (B) TYPE: amino acid
        (D) TOPOLOGY: linear (ii) MOLECULE TYPE: protein (xi) SEQUENCE DESCRIPTION: SEQ ID NO: 30:

```
Met Met Ser Thr Tyr Lys Arg Pro Thr Leu Asp Glu Glu Asp Leu Val
 1               5                  10                  15

Asp Ser Leu Ser Glu Ser Asp Val Tyr Pro Asn His Leu Gln Val Asn
            20                  25                  30

Phe Arg Gly Pro Arg Asn Gly Gln Arg Cys Trp Ala Ala Arg Thr Pro
        35                  40                  45

Val Glu Lys Arg Leu Val Val Leu Val Ala Leu Leu Ala Ala Ala Leu
    50                  55                  60

Val Ala Cys Leu Ala Val Leu Gly Ile Gln Tyr Gln Thr Arg Thr Pro
65                  70                  75                  80

Ser Val Cys Leu Ser Glu Ala Cys Ile Ser Val Thr Ser Ser Ile Leu
                85                  90                  95

Ser Ser Met Asp Pro Thr Val Asp Pro Cys Gln Asp Phe Phe Thr Tyr
            100                 105                 110

Ala Cys Gly Gly Trp Ile Lys Ala Asn Pro Val Pro Asp Gly His Ser
        115                 120                 125

Arg Trp Gly Thr Phe Ser Asn Leu Trp Glu His Asn Gln Ala Ile Ile
    130                 135                 140

Lys His Leu Leu Glu Asn Ser Thr Ala Ser Val Ser Glu Ala Glu Arg
145                 150                 155                 160

Lys Asp Gln Glu Tyr Tyr Arg Ala Cys Met Asn Glu Thr Arg Ile Glu
                165                 170                 175

Glu Leu Lys Ala Lys Pro Leu Met Glu Leu Ile Glu Lys Leu Gly Gly
            180                 185                 190

Trp Asn Ile Thr Gly Pro Trp Asp Lys Asp Asn Phe Gln Asp Thr Leu
        195                 200                 205

Gln Val Val Thr Ser His Tyr His Thr Ser Pro Phe Phe Ser Val Tyr
    210                 215                 220

Val Ser Ala Asp Ser Lys Asn Ser Asn Ser Asn Val Ile Gln Val Asp
225                 230                 235                 240
```

-continued

```
Gln Ser Gly Leu Gly Leu Pro Ser Arg Asp Tyr Tyr Leu Asn Lys Thr
            245                 250                 255

Glu Asn Glu Lys Val Leu Thr Gly Tyr Leu Asn Tyr Met Val Gln Leu
        260                 265                 270

Gly Lys Leu Leu Gly Gly Ala Glu Asp Thr Ile Arg Pro Gln Met
        275                 280             285

Gln Gln Ile Leu Asp Phe Glu Thr Ala Leu Ala Asn Ile Thr Ile Pro
        290                 295                 300

Gln Glu Lys Arg Arg Asp Glu Leu Ile Tyr His Lys Val Thr Ala
305                 310                 315                 320

Ala Glu Leu Gln Thr Leu Ala Pro Ala Ile Asn Trp Leu Pro Phe Leu
                325                 330                 335

Asn Thr Ile Phe Tyr Pro Val Glu Ile Asn Glu Ser Glu Pro Ile Val
                340                 345                 350

Ile Tyr Asp Lys Glu Tyr Leu Ser Lys Val Ser Thr Leu Ile Asn Ser
            355                 360                 365

Thr Asp Lys Cys Leu Leu Asn Asn Tyr Met Ile Trp Asn Leu Val Arg
370                 375                 380

Lys Thr Ser Ser Phe Leu Asp Gln Arg Phe Gln Asp Ala Asp Glu Lys
385                 390                 395                 400

Phe Met Glu Val Met Tyr Gly Thr Lys Lys Thr Cys Leu Pro Arg Trp
                405                 410                 415

Lys Phe Cys Val Ser Asp Thr Glu Asn Thr Leu Gly Phe Ala Leu Gly
                420                 425                 430

Pro Met Phe Val Lys Ala Thr Phe Ala Glu Asp Ser Lys Asn Ile Ala
            435                 440                 445

Ser Glu Ile Ile Leu Glu Ile Lys Lys Ala Phe Glu Glu Ser Leu Ser
450                 455                 460

Thr Leu Lys Trp Met Asp Glu Asp Thr Arg Lys Ser Ala Lys Glu Lys
465                 470                 475                 480

Ala Asp Ala Ile Tyr Asn Met Ile Gly Tyr Pro Asn Phe Ile Met Asp
                485                 490                 495

Pro Lys Glu Leu Asp Lys Val Phe Asn Asp Tyr Thr Ala Val Pro Asp
            500                 505                 510

Leu Tyr Phe Glu Asn Ala Met Arg Phe Phe Asn Phe Ser Trp Arg Val
            515                 520                 525

Thr Ala Asp Gln Leu Arg Lys Ala Pro Asn Arg Asp Gln Trp Ser Met
            530                 535                 540

Thr Pro Pro Met Val Asn Ala Tyr Tyr Ser Pro Thr Lys Asn Glu Ile
545                 550                 555                 560

Val Phe Pro Ala Gly Ile Leu Gln Ala Pro Phe Tyr Thr Arg Ser Ser
                565                 570                 575

Pro Asn Ala Leu Asn Phe Gly Gly Ile Gly Val Val Gly His Glu
            580                 585                 590

Leu Thr His Ala Phe Asp Asp Gln Gly Arg Glu Tyr Asp Lys Asp Gly
                595                 600                 605

Asn Leu Arg Pro Trp Trp Lys Asn Ser Ser Val Glu Ala Phe Lys Gln
            610                 615                 620

Gln Thr Ala Cys Met Val Glu Gln Tyr Gly Asn Tyr Ser Val Asn Gly
625                 630                 635                 640

Glu Pro Val Asn Gly Arg His Thr Leu Gly Glu Asn Ile Ala Asp Asn
                645                 650                 655
```

```
Gly Gly Leu Lys Ala Ala Tyr Arg Ala Tyr Gln Asn Trp Val Lys Lys
            660                 665                 670

Asn Gly Ala Glu Gln Thr Leu Pro Thr Leu Gly Leu Thr Asn Asn Gln
            675                 680                 685

Leu Phe Phe Leu Ser Phe Ala Gln Val Trp Cys Ser Val Arg Thr Pro
690                 695                 700

Glu Ser Ser His Glu Gly Leu Ile Thr Asp Pro His Ser Pro Ser Arg
705                 710                 715                 720

Phe Arg Val Ile Gly Ser Ile Ser Asn Ser Lys Glu Phe Ser Glu His
                725                 730                 735

Phe His Cys Pro Pro Gly Ser Pro Met Asn Pro His His Lys Cys Glu
            740                 745                 750

Val Trp (2) INFORMATION FOR SEQ ID NO: 31:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 31:

GAGAGAGAGA GAGAGAGAGA ACTAGTCTCG AGCCAAGCAG GCCACCAGTC CTG         53

(2) INFORMATION FOR SEQ ID NO: 32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 32:

CCTGCCGCCA GAAGTACCAC CAACA                                        25

(2) INFORMATION FOR SEQ ID NO: 33:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (ii) MOLECULE TYPE: cDNA for mRNA (xi) SEQUENCE DESCRIPTION: SEQ ID NO: 33:

CGCCCCCCCG GTGTCCGCCC TGCTGTCGGC GCTGGGG ATG TCG ACG TAC AAG CGG    55
                                         Met Ser Thr Tyr Lys Arg
                                           1               5

GCC ACG CTG GAC GAG GAG GAC CTG GTG GAC TCG CTC TCC GAG GGC GAC    103
Ala Thr Leu Asp Glu Glu Asp Leu Val Asp Ser Leu Ser Glu Gly Asp
            10                  15                  20

GCA TAC CCC AAC GGC CTG CAG GTG AAC TTC CAC AGC CCC CGG AGT GGC    151
Ala Tyr Pro Asn Gly Leu Gln Val Asn Phe His Ser Pro Arg Ser Gly
            25                  30                  35

CAG AGG TGC TGG GCT GCA CGG ACC CAG GTG GAG AAG CGG CTG GTG GTG    199
Gln Arg Cys Trp Ala Ala Arg Thr Gln Val Glu Lys Arg Leu Val Val
        40                  45                  50
```

```
TTG GTG GTA CTT CTG GCG GCA GG                                                222
Leu Val Val Leu Leu Ala Ala
 55                  60

(2) INFORMATION FOR SEQ ID NO: 34:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO: 34:

Met Ser Thr Tyr Lys Arg Ala Thr Leu Asp Glu Glu Asp Leu Val Asp
 1               5                  10                  15

Ser Leu Ser Glu Gly Asp Ala Tyr Pro Asn Gly Leu Gln Val Asn Phe
            20                  25                  30

His Ser Pro Arg Ser Gly Gln Arg Cys Trp Ala Ala Arg Thr Gln Val
        35                  40                  45

Glu Lys Arg Leu Val Val Leu Val Val Leu Leu Ala Ala
     50                  55                  60

(2) INFORMATION FOR SEQ ID NO: 35:

(i) SEQUENCE CHARACTERISTICS:
        (A) LENGTH: 2720 base pairs
        (B) TYPE: nucleic acid
        (C) STRANDEDNESS: single
        (D) TOPOLOGY: linear (ii) MOLECULE TYPE: cDNA for mRNA (xi) SEQUENCE DESCRIPTION: SEQ ID NO: 35:

CGCCCCCCCG GTGTCCGCCC TGCTGTCGGC GCTGGGG ATG TCG ACG TAC AAG CGG          55
                                        Met Ser Thr Tyr Lys Arg
                                         1                   5

GCC ACG CTG GAC GAG GAG GAC CTG GTG GAC TCG CTC TCC GAG GGC GAC          103
Ala Thr Leu Asp Glu Glu Asp Leu Val Asp Ser Leu Ser Glu Gly Asp
            10                  15                  20

GCA TAC CCC AAC GGC CTG CAG GTG AAC TTC CAC AGC CCC CGG AGT GGC          151
Ala Tyr Pro Asn Gly Leu Gln Val Asn Phe His Ser Pro Arg Ser Gly
        25                  30                  35

CAG AGG TGC TGG GCT GCA CGG ACC CAG GTG GAG AAG CGG CTG GTG GTG          199
Gln Arg Cys Trp Ala Ala Arg Thr Gln Val Glu Lys Arg Leu Val Val
     40                  45                  50

TTG GTG GTA CTT CTG GCG GCA GGA CTG GTG GCC TGC TTG GCA GCA CTG          247
Leu Val Val Leu Leu Ala Ala Gly Leu Val Ala Cys Leu Ala Ala Leu
 55                  60                  65                  70

GGC ATC CAG TAC CAG ACA AGA TCC CCC TCT GTG TGC CTG AGC GAA GCT          295
Gly Ile Gln Tyr Gln Thr Arg Ser Pro Ser Val Cys Leu Ser Glu Ala
                 75                  80                  85

TGT GTC TCA GTG ACC AGC TCC ATC TTG AGC TCC ATG GAC CCC ACA GTG          343
Cys Val Ser Val Thr Ser Ser Ile Leu Ser Ser Met Asp Pro Thr Val
                 90                  95                 100

GAC CCC TGC CAT GAC TTC TTC AGC TAC GCC TGT GGG GGC TGG ATC AAG          391
Asp Pro Cys His Asp Phe Phe Ser Tyr Ala Cys Gly Gly Trp Ile Lys
            105                 110                 115

GCC AAC CCA GTC CCT GAT GGC CAC TCA CGC TGG GGG ACC TTC AGC AAC          439
Ala Asn Pro Val Pro Asp Gly His Ser Arg Trp Gly Thr Phe Ser Asn
        120                 125                 130

CTC TGG GAA CAC AAC CAA GCA ATC ATC AAG CAC CTC CTC GAA AAC TCC          487
Leu Trp Glu His Asn Gln Ala Ile Ile Lys His Leu Leu Glu Asn Ser
```

-continued

| | | | | | | | | | | | | | | | |
|---|---|---|---|---|---|---|---|---|---|---|---|---|---|---|---|
| 135 | | | | | 140 | | | | | 145 | | | | 150 | |
| ACG | GCC | AGC | GTG | AGC | GAG | GCA | GAG | AGA | AAG | GCG | CAA | GTA | TAC | TAC | CGT | 535 |
| Thr | Ala | Ser | Val | Ser | Glu | Ala | Glu | Arg | Lys | Ala | Gln | Val | Tyr | Tyr | Arg |
| | | | 155 | | | | | 160 | | | | | 165 | | |
| GCG | TGC | ATG | AAC | GAG | ACC | AGG | ATC | GAG | GAG | CTC | AGG | GCC | AAA | CCT | CTA | 583 |
| Ala | Cys | Met | Asn | Glu | Thr | Arg | Ile | Glu | Glu | Leu | Arg | Ala | Lys | Pro | Leu |
| | | | 170 | | | | | 175 | | | | | 180 | | |
| ATG | GAG | TTG | ATT | GAG | AGG | CTC | GGG | GGC | TGG | AAC | ATC | ACA | GGT | CCC | TGG | 631 |
| Met | Glu | Leu | Ile | Glu | Arg | Leu | Gly | Gly | Trp | Asn | Ile | Thr | Gly | Pro | Trp |
| | | | 185 | | | | | 190 | | | | | 195 | | |
| GCC | AAG | GAC | AAC | TTC | CAG | GAC | ACC | CTG | CAG | GTG | GTC | ACC | GCC | CAC | TAC | 679 |
| Ala | Lys | Asp | Asn | Phe | Gln | Asp | Thr | Leu | Gln | Val | Val | Thr | Ala | His | Tyr |
| | | | 200 | | | | | 205 | | | | | 210 | | |
| CGC | ACC | TCA | CCC | TTC | TTC | TCT | GTC | TAT | GTC | AGT | GCC | GAT | TCC | AAG | AAC | 727 |
| Arg | Thr | Ser | Pro | Phe | Phe | Ser | Val | Tyr | Val | Ser | Ala | Asp | Ser | Lys | Asn |
| 215 | | | | | 220 | | | | | 225 | | | | | 230 |
| TCC | AAC | AGC | AAC | GTG | ATC | CAG | GTG | GAC | CAG | TCT | GGC | CTG | GGC | TTG | CCC | 775 |
| Ser | Asn | Ser | Asn | Val | Ile | Gln | Val | Asp | Gln | Ser | Gly | Leu | Gly | Leu | Pro |
| | | | 235 | | | | | 240 | | | | | 245 | | |
| TCG | AGA | GAC | TAT | TAC | CTG | AAC | AAA | ACT | GAA | AAC | GAG | AAG | GTG | CTG | ACC | 823 |
| Ser | Arg | Asp | Tyr | Tyr | Leu | Asn | Lys | Thr | Glu | Asn | Glu | Lys | Val | Leu | Thr |
| | | | 250 | | | | | 255 | | | | | 260 | | |
| GGA | TAT | CTG | AAC | TAC | ATG | GTC | CAG | CTG | GGG | AAG | CTG | CTG | GGC | GGC | GGG | 871 |
| Gly | Tyr | Leu | Asn | Tyr | Met | Val | Gln | Leu | Gly | Lys | Leu | Leu | Gly | Gly | Gly |
| | | | 265 | | | | | 270 | | | | | 275 | | |
| GAC | GAG | GAG | GCC | ATC | CGG | CCC | CAG | ATG | CAG | CAG | ATC | TTG | GAC | TTT | GAG | 919 |
| Asp | Glu | Glu | Ala | Ile | Arg | Pro | Gln | Met | Gln | Gln | Ile | Leu | Asp | Phe | Glu |
| | | | 280 | | | | | 285 | | | | | 290 | | |
| ACG | GCA | CTG | GCC | AAC | ATC | ACC | ATC | CCA | CAG | GAG | AAG | CGC | CGT | GAT | GAG | 967 |
| Thr | Ala | Leu | Ala | Asn | Ile | Thr | Ile | Pro | Gln | Glu | Lys | Arg | Arg | Asp | Glu |
| 295 | | | | | 300 | | | | | 305 | | | | | 310 |
| GAG | CTC | ATC | TAC | CAC | AAA | GTG | ACG | GCA | GCC | GAG | CTG | CAG | ACC | TTG | GCA | 1015 |
| Glu | Leu | Ile | Tyr | His | Lys | Val | Thr | Ala | Ala | Glu | Leu | Gln | Thr | Leu | Ala |
| | | | 315 | | | | | 320 | | | | | 325 | | |
| CCC | GCC | ATC | AAC | TGG | TTG | CCT | TTT | CTC | AAC | ACC | ATC | TTC | TAC | CCC | GTG | 1063 |
| Pro | Ala | Ile | Asn | Trp | Leu | Pro | Phe | Leu | Asn | Thr | Ile | Phe | Tyr | Pro | Val |
| | | | 330 | | | | | 335 | | | | | 340 | | |
| GAG | ATC | AAT | GAA | TCC | GAG | CCT | ATT | GTG | GTC | TAT | GAC | AAG | GAA | TAC | CTT | 1111 |
| Glu | Ile | Asn | Glu | Ser | Glu | Pro | Ile | Val | Val | Tyr | Asp | Lys | Glu | Tyr | Leu |
| | | | 345 | | | | | 350 | | | | | 355 | | |
| GAG | CAG | ATC | TCC | ACT | CTC | ATC | AAC | ACC | ACC | GAC | AGA | TGC | CTG | CTC | AAC | 1159 |
| Glu | Gln | Ile | Ser | Thr | Leu | Ile | Asn | Thr | Thr | Asp | Arg | Cys | Leu | Leu | Asn |
| | | | 360 | | | | | 365 | | | | | 370 | | |
| AAC | TAC | ATG | ATC | TGG | AAC | CTG | GTG | CGG | AAA | ACA | AGC | TCC | TTC | CTT | GAC | 1207 |
| Asn | Tyr | Met | Ile | Trp | Asn | Leu | Val | Arg | Lys | Thr | Ser | Ser | Phe | Leu | Asp |
| 375 | | | | | 380 | | | | | 385 | | | | | 390 |
| CAG | CGC | TTT | CAG | GAC | GCC | GAT | GAG | AAG | TTC | ATG | GAA | GTC | ATG | TAC | GGG | 1255 |
| Gln | Arg | Phe | Gln | Asp | Ala | Asp | Glu | Lys | Phe | Met | Glu | Val | Met | Tyr | Gly |
| | | | 395 | | | | | 400 | | | | | 405 | | |
| ACC | AAG | AAG | ACC | TGT | CTT | CCT | CGC | TGG | AAG | TTT | TGC | GTG | AGT | GAC | ACA | 1303 |
| Thr | Lys | Lys | Thr | Cys | Leu | Pro | Arg | Trp | Lys | Phe | Cys | Val | Ser | Asp | Thr |
| | | | 410 | | | | | 415 | | | | | 420 | | |
| GAA | AAC | AAC | CTG | GGC | TTT | GCG | TTG | GGC | CCC | ATG | TTT | GTC | AAA | GCA | ACC | 1351 |
| Glu | Asn | Asn | Leu | Gly | Phe | Ala | Leu | Gly | Pro | Met | Phe | Val | Lys | Ala | Thr |
| | | | 425 | | | | | 430 | | | | | 435 | | |
| TTC | GCC | GAG | GAC | AGC | AAG | AGC | ATA | GCC | ACC | GAG | ATC | ATC | CTG | GAG | ATT | 1399 |
| Phe | Ala | Glu | Asp | Ser | Lys | Ser | Ile | Ala | Thr | Glu | Ile | Ile | Leu | Glu | Ile |
| | | | 440 | | | | | 445 | | | | | 450 | | |
| AAG | AAG | GCA | TTT | GAG | GAA | AGC | CTG | AGC | ACC | CTG | AAG | TGG | ATG | GAT | GAG | 1447 |

```
Lys Lys Ala Phe Glu Glu Ser Leu Ser Thr Leu Lys Trp Met Asp Glu
455                 460                 465                 470

GAA ACC CGA AAA TCA GCC AAG GAA AAG GCC GAT GCC ATC TAC AAC ATG    1495
Glu Thr Arg Lys Ser Ala Lys Glu Lys Ala Asp Ala Ile Tyr Asn Met
                475                 480                 485

ATA GGA TAC CCC AAC TTC ATC ATG GAT CCC AAG GAG CTG GAC AAA GTG    1543
Ile Gly Tyr Pro Asn Phe Ile Met Asp Pro Lys Glu Leu Asp Lys Val
                    490                 495                 500

TTT AAT GAC TAC ACT GCA GTT CCA GAC CTC TAC TTT GAA AAT GCC ATG    1591
Phe Asn Asp Tyr Thr Ala Val Pro Asp Leu Tyr Phe Glu Asn Ala Met
                505                 510                 515

CGG TTT TTC AAC TTC TCA TGG AGG GTC ACT GCC GAT CAG CTC AGG AAA    1639
Arg Phe Phe Asn Phe Ser Trp Arg Val Thr Ala Asp Gln Leu Arg Lys
                520                 525                 530

GCC CCC AAC AGA GAT CAG TGG AGC ATG ACC CCG CCC ATG GTG AAC GCC    1687
Ala Pro Asn Arg Asp Gln Trp Ser Met Thr Pro Pro Met Val Asn Ala
535                 540                 545                 550

TAC TAC TCG CCC ACC AAG AAT GAG ATT GTG TTT CCG GCC GGG ATC CTG    1735
Tyr Tyr Ser Pro Thr Lys Asn Glu Ile Val Phe Pro Ala Gly Ile Leu
                555                 560                 565

CAG GCA CCA TTC TAC ACA CGC TCC TCA CCC AAG GCC TTA AAC TTT GGT    1783
Gln Ala Pro Phe Tyr Thr Arg Ser Ser Pro Lys Ala Leu Asn Phe Gly
                570                 575                 580

GGC ATA GGT GTC GTC GTG GGC CAT GAG CTG ACT CAT GCT TTT GAT GAT    1831
Gly Ile Gly Val Val Val Gly His Glu Leu Thr His Ala Phe Asp Asp
                585                 590                 595

CAA GGA CGG GAG TAT GAC AAG GAC GGG AAC CTC CGG CCA TGG TGG AAG    1879
Gln Gly Arg Glu Tyr Asp Lys Asp Gly Asn Leu Arg Pro Trp Trp Lys
600                 605                 610

AAC TCA TCC GTG GAG GCC TTC AAG CGT CAG ACC GAG TGC ATG GTA GAG    1927
Asn Ser Ser Val Glu Ala Phe Lys Arg Gln Thr Glu Cys Met Val Glu
615                 620                 625                 630

CAG TAC AGC AAC TAC AGC GTG AAC GGG GAG CCG GTG AAC GGG CGG CAC    1975
Gln Tyr Ser Asn Tyr Ser Val Asn Gly Glu Pro Val Asn Gly Arg His
                635                 640                 645

ACC CTG GGG GAG AAC ATC GCC GAC AAC GGG GGT CTC AAG GCG GCC TAT    2023
Thr Leu Gly Glu Asn Ile Ala Asp Asn Gly Gly Leu Lys Ala Ala Tyr
                650                 655                 660

CGG GCT TAC CAG AAC TGG GTG AAG AAG AAC GGG GCT GAG CAC TCG CTC    2071
Arg Ala Tyr Gln Asn Trp Val Lys Lys Asn Gly Ala Glu His Ser Leu
                665                 670                 675

CCC ACC CTG GGC CTC ACC AAT AAC CAG CTC TTC TTC CTG GGC TTT GCA    2119
Pro Thr Leu Gly Leu Thr Asn Asn Gln Leu Phe Phe Leu Gly Phe Ala
                680                 685                 690

CAG GTC TGG TGC TCC GTC CGC ACA CCT GAG AGC TCC CAC GAA GGC CTC    2167
Gln Val Trp Cys Ser Val Arg Thr Pro Glu Ser Ser His Glu Gly Leu
695                 700                 705                 710

ATC ACC GAT CCC CAC AGC CCC TCT CGC TTC CGG GTC ATC GGC TCC CTC    2215
Ile Thr Asp Pro His Ser Pro Ser Arg Phe Arg Val Ile Gly Ser Leu
                715                 720                 725

TCC AAT TCC AAG GAG TTC TCA GAA CAC TTC CGC TGC CCA CCT GGC TCA    2263
Ser Asn Ser Lys Glu Phe Ser Glu His Phe Arg Cys Pro Pro Gly Ser
                730                 735                 740

CCC ATG AAC CCG CCT CAC AAG TGC GAA GTC TGG T AAGGACGAAG           2307
Pro Met Asn Pro Pro His Lys Cys Glu Val Trp
                745                 750

CGGAGAGAGC CAAGCGGAG GAGGGGAAGG GGCTGAGGAC GAGACCCCCA TCCAGCCTCC   2367

AGGGCATTGC TCAGCCCGCT TGGCCACCCG GGGCCCTGCT TCCTCACACT GGCGGGTTTT  2427
```

```
CAGCCGGAAC CGAGCCCATG GTGTTGGCTC TCAACGTGAC CCGCAGTCTG ATCCCCTGTG    2487

AAGAGCCGGA CATCCCAGGC ACACGTGTGC GCCACCTTCA GCAGGCATTC GGGTGCTGGG    2547

CTGGTGGCTC ATCAGGCCTG GGCCCCACAC TGACAAGCGC CAGATACGCC ACAAATACCA    2607

CTGTGTCAAA TGCTTTCAAG ATATATTTTT GGGGAAACTA TTTTTTAAAC ACTGTGGAAT    2667

ACACTGGAAA TCTTCAGGGA AAAACACATT TAAACACTTT TTTTTTTAAG CCC           2720
```

(2) INFORMATION FOR SEQ ID NO: 36:

(i) SEQUENCE CHARACTERISTICS:
        (A) LENGTH: 753 amino acids
        (B) TYPE: amino acid
        (D) TOPOLOGY: linear (ii) MOLECULE TYPE: protein (xi) SEQUENCE DESCRIPTION: SEQ ID NO: 36:

```
Met Ser Thr Tyr Lys Arg Ala Thr Leu Asp Glu Glu Asp Leu Val Asp
  1               5                  10                  15

Ser Leu Ser Glu Gly Asp Ala Tyr Pro Asn Gly Leu Gln Val Asn Phe
                 20                  25                  30

His Ser Pro Arg Ser Gly Gln Arg Cys Trp Ala Ala Arg Thr Gln Val
             35                  40                  45

Glu Lys Arg Leu Val Val Leu Val Leu Leu Ala Ala Gly Leu Val
 50                  55                  60

Ala Cys Leu Ala Ala Leu Gly Ile Gln Tyr Gln Thr Arg Ser Pro Ser
 65                  70                  75                  80

Val Cys Leu Ser Glu Ala Cys Val Ser Val Thr Ser Ser Ile Leu Ser
                 85                  90                  95

Ser Met Asp Pro Thr Val Asp Pro Cys His Asp Phe Phe Ser Tyr Ala
                100                 105                 110

Cys Gly Gly Trp Ile Lys Ala Asn Pro Val Pro Asp Gly His Ser Arg
            115                 120                 125

Trp Gly Thr Phe Ser Asn Leu Trp Glu His Asn Gln Ala Ile Ile Lys
        130                 135                 140

His Leu Leu Glu Asn Ser Thr Ala Ser Val Ser Glu Ala Glu Arg Lys
145                 150                 155                 160

Ala Gln Val Tyr Tyr Arg Ala Cys Met Asn Glu Thr Arg Ile Glu Glu
                165                 170                 175

Leu Arg Ala Lys Pro Leu Met Glu Leu Ile Glu Arg Leu Gly Gly Trp
            180                 185                 190

Asn Ile Thr Gly Pro Trp Ala Lys Asp Asn Phe Gln Asp Thr Leu Gln
        195                 200                 205

Val Val Thr Ala His Tyr Arg Thr Ser Pro Phe Phe Ser Val Tyr Val
    210                 215                 220

Ser Ala Asp Ser Lys Asn Ser Asn Ser Asn Val Ile Gln Val Asp Gln
225                 230                 235                 240

Ser Gly Leu Gly Leu Pro Ser Arg Asp Tyr Tyr Leu Asn Lys Thr Glu
                245                 250                 255

Asn Glu Lys Val Leu Thr Gly Tyr Leu Asn Tyr Met Val Gln Leu Gly
            260                 265                 270

Lys Leu Leu Gly Gly Gly Asp Glu Glu Ala Ile Arg Pro Gln Met Gln
        275                 280                 285

Gln Ile Leu Asp Phe Glu Thr Ala Leu Ala Asn Ile Thr Ile Pro Gln
    290                 295                 300
```

-continued

| | | | | | | | | | | | | | | | |
|---|---|---|---|---|---|---|---|---|---|---|---|---|---|---|---|
| Glu | Lys | Arg | Arg | Asp | Glu | Glu | Leu | Ile | Tyr | His | Lys | Val | Thr | Ala | Ala |
| 305 | | | | 310 | | | | | 315 | | | | | 320 | |
| Glu | Leu | Gln | Thr | Leu | Ala | Pro | Ala | Ile | Asn | Trp | Leu | Pro | Phe | Leu | Asn |
| | | | | 325 | | | | | 330 | | | | | 335 | |
| Thr | Ile | Phe | Tyr | Pro | Val | Glu | Ile | Asn | Glu | Ser | Glu | Pro | Ile | Val | Val |
| | | | | 340 | | | | | 345 | | | | | 350 | |
| Tyr | Asp | Lys | Glu | Tyr | Leu | Glu | Gln | Ile | Ser | Thr | Leu | Ile | Asn | Thr | Thr |
| | | | 355 | | | | | 360 | | | | | 365 | | |
| Asp | Arg | Cys | Leu | Leu | Asn | Asn | Tyr | Met | Ile | Trp | Asn | Leu | Val | Arg | Lys |
| | | 370 | | | | | 375 | | | | | 380 | | | |
| Thr | Ser | Ser | Phe | Leu | Asp | Gln | Arg | Phe | Gln | Asp | Ala | Asp | Glu | Lys | Phe |
| 385 | | | | | 390 | | | | | 395 | | | | | 400 |
| Met | Glu | Val | Met | Tyr | Gly | Thr | Lys | Lys | Thr | Cys | Leu | Pro | Arg | Trp | Lys |
| | | | | 405 | | | | | 410 | | | | | 415 | |
| Phe | Cys | Val | Ser | Asp | Thr | Glu | Asn | Asn | Leu | Gly | Phe | Ala | Leu | Gly | Pro |
| | | | 420 | | | | | 425 | | | | | 430 | | |
| Met | Phe | Val | Lys | Ala | Thr | Phe | Ala | Glu | Asp | Ser | Lys | Ser | Ile | Ala | Thr |
| | | | 435 | | | | | 440 | | | | | 445 | | |
| Glu | Ile | Ile | Leu | Glu | Ile | Lys | Lys | Ala | Phe | Glu | Glu | Ser | Leu | Ser | Thr |
| | | 450 | | | | | 455 | | | | | 460 | | | |
| Leu | Lys | Trp | Met | Asp | Glu | Glu | Thr | Arg | Lys | Ser | Ala | Lys | Glu | Lys | Ala |
| 465 | | | | | 470 | | | | | 475 | | | | | 480 |
| Asp | Ala | Ile | Tyr | Asn | Met | Ile | Gly | Tyr | Pro | Asn | Phe | Ile | Met | Asp | Pro |
| | | | | 485 | | | | | 490 | | | | | 495 | |
| Lys | Glu | Leu | Asp | Lys | Val | Phe | Asn | Asp | Tyr | Thr | Ala | Val | Pro | Asp | Leu |
| | | | 500 | | | | | 505 | | | | | 510 | | |
| Tyr | Phe | Glu | Asn | Ala | Met | Arg | Phe | Phe | Asn | Phe | Ser | Trp | Arg | Val | Thr |
| | | | 515 | | | | | 520 | | | | | 525 | | |
| Ala | Asp | Gln | Leu | Arg | Lys | Ala | Pro | Asn | Arg | Asp | Gln | Trp | Ser | Met | Thr |
| | | 530 | | | | | 535 | | | | | 540 | | | |
| Pro | Pro | Met | Val | Asn | Ala | Tyr | Tyr | Ser | Pro | Thr | Lys | Asn | Glu | Ile | Val |
| 545 | | | | | 550 | | | | | 555 | | | | | 560 |
| Phe | Pro | Ala | Gly | Ile | Leu | Gln | Ala | Pro | Phe | Tyr | Thr | Arg | Ser | Ser | Pro |
| | | | | 565 | | | | | 570 | | | | | 575 | |
| Lys | Ala | Leu | Asn | Phe | Gly | Gly | Ile | Gly | Val | Val | Gly | His | Glu | Leu |
| | | | 580 | | | | | 585 | | | | | 590 | | |
| Thr | His | Ala | Phe | Asp | Asp | Gln | Gly | Arg | Glu | Tyr | Asp | Lys | Asp | Gly | Asn |
| | | | 595 | | | | | 600 | | | | | 605 | | |
| Leu | Arg | Pro | Trp | Trp | Lys | Asn | Ser | Val | Glu | Ala | Phe | Lys | Arg | Gln |
| | 610 | | | | | 615 | | | | | 620 | | | | |
| Thr | Glu | Cys | Met | Val | Glu | Gln | Tyr | Ser | Asn | Tyr | Ser | Val | Asn | Gly | Glu |
| 625 | | | | | 630 | | | | | 635 | | | | | 640 |
| Pro | Val | Asn | Gly | Arg | His | Thr | Leu | Gly | Glu | Asn | Ile | Ala | Asp | Asn | Gly |
| | | | | 645 | | | | | 650 | | | | | 655 | |
| Gly | Leu | Lys | Ala | Ala | Tyr | Arg | Ala | Tyr | Gln | Asn | Trp | Val | Lys | Lys | Asn |
| | | | 660 | | | | | 665 | | | | | 670 | | |
| Gly | Ala | Glu | His | Ser | Leu | Pro | Thr | Leu | Gly | Leu | Thr | Asn | Asn | Gln | Leu |
| | | | 675 | | | | | 680 | | | | | 685 | | |
| Phe | Phe | Leu | Gly | Phe | Ala | Gln | Val | Trp | Cys | Ser | Val | Arg | Thr | Pro | Glu |
| | | | 690 | | | | | 695 | | | | | 700 | | |
| Ser | Ser | His | Glu | Gly | Leu | Ile | Thr | Asp | Pro | His | Ser | Pro | Ser | Arg | Phe |
| 705 | | | | 710 | | | | | 715 | | | | | 720 | |
| Arg | Val | Ile | Gly | Ser | Leu | Ser | Asn | Ser | Lys | Glu | Phe | Ser | Glu | His | Phe |

```
                    725                 730                 735
Arg Cys Pro Pro Gly Ser Pro Met Asn Pro Pro His Lys Cys Glu Val
                740                 745                 750
Trp
```

ENDOTHELIN CONVERTING ENZYME (ECE)

This is a 371 of international application no. PCT/EP94/03706 filed on Nov. 10, 1994.

The present invention relates to endothelin converting enzymes, to processes for their preparation and to their use.

Elevated endothelin levels are thought to be associated with a large number of disorders such as essential hypertension, myocardial infarct, acute kidney failure, shock or heart failure. An association of this type is also suggested by the results obtainable with endothelin antibodies. In animal models it was possible therewith to reduce the size of a myocardial infarct dose-dependently (Watanabe et al., Nature 344, 114 (1990)), to have a beneficial effect on kidney function (Kon et al., J. Clin. Invest. 83, 1762 (1989)), and to reduce the nephrotoxicity of cyclosporin (Kon et al., Kidney Int. 37, 1487 (1990)).

Endothelin converting enzyme (ECE-1) liberates endothelin 1 from the precursor molecule big endothelin 1 which consists of 38 amino acids. The unwanted biological effects caused by endothelin 1 can be counteracted, for example, by inhibiting endothelin converting enzyme and thus endothelin 1 biosynthesis.

Enzyme activities which liberate endothelins or endothelin-like molecules from the corresponding precursor molecules, the big endothelins, have been isolated from various cell lines (Takeda et al., Biochem. Biophys. Res. Comm. 176, 860 (1991), Ohnaka et al., Biochem. Biophys. Res. Comm. 168, 1128 (1990); Matsumura et al. FEBS Lett. 293, 45 (1992), Ahn et al. Proc. Natl. Acad. Sci. U.S.A. 89, 8606 (1992), PCT WO 92/13944, Ohnaka et al. Clin. Exp. Hypertension A 14; No. 4 (1992), Okada et al. Biochem. Biophys. Res. Comm. 180, 1019 (1991), Takada et al. Biochem. Biophys. Res. Comm. 182, 1383 (1992), Opgenorth et. al. FASEB 6, 2653 (1992)).

However, these enzyme activities have not to date been adequately characterized. They are in the form of enzyme mixtures which have not been greatly concentrated. However, impure enzyme mixtures of these types are not very suitable for use in assay methods for finding specific ECE inhibitors because foreign proteases which are of no physiological relevance considerably interfere with the enzyme assay.

Thus, big endothelin is cleaved, for example, also by the serine protease chymothrypsin [sic] as well as by papain, thermolysin and NEP 24.11 to endothelin and endothelin-like products which are incorrectly assigned to the enzyme ECE in assay methods. As a consequence, there are contradictions in the description of endothelin converting enzyme in the literature.

The statements about the molecular weight of endothelin converting enzyme vary from 65 KDalton to 540 KDalton; the statements about Km and vmax values likewise differ considerably from one another (Opgenorth et al. FASEB 6, 2653 (1992); Sawamura et al. Biochem. Biophys. Acta 1161,295 (1993)). There are also contradictions about whether endothelin converting enzyme is to be assigned to the family of aspartate proteases or of metalloproteases (Sawamura et al. Biochem. Biophys. Acta 1161,295 (1993); Biochem. Pharmacol. 43,845 (1992). Furthermore, contradictory statements about characteristic information as to whether the metalloprotease is a cytoplasmic or membrane-bound enzyme, and which substrates are converted by the particular ECE (big Et-1; big Et-3), are to be found in the literature: Matsumura et al. (FEBS Lett. 293, 45 (1992)): Takahashi et al. (J. Biol. Chem. 268;21394 (1993)); Okada et al. (Biochem. Biophys. Res. Comm. 180, 1019 (1991)); Ohnaka et al. (Clin. Exp. Hypertension A 14; No. 4 (1992)); Matsumura et al. (FEBS Lett. 305;86 (1992)).

To date no unambiguous description of ECE making it possible satisfactorily to define ECE has been shown. Such a definition may be possible only through determination of the primary structure, of the amino acid sequence, of ECE. For this it is necessary first to prepare ECE in pure form.

It is an object of the present invention to prepare endothelin converting enzyme in pure form.

We have found that this object is achieved by an endothelin converting enzyme having a molecular weight of 250,000 Dalton and the partial amino acid sequence SEQ ID NO: 1.

The endothelin converting enzyme according to the invention has the following features: it has a molecular weight of about 250,000 Dalton determined by SDS polyacrylamide gel electrophoresis under non-reducing conditions.

Under reducing conditions in SDS polyacrylamide gel electrophoresis it shows a band of about 125,000 Dalton; it presumably consists of a homodimer.

Endothelin converting enzyme is glycosylated. Enzymatic removal of the sugar residues alters the apparent molecular weight from 125,000 Dalton to about 82,000 Dalton.

Sequencing of tryptic peptides of endothelin converting enzyme provides the following partial amino acid sequences SEQ ID NO: 1,2,3,4,5,6.

Further characterization of the endothelin converting enzyme according to the invention is undertaken in the examples.

The invention furthermore relates to endothelin converting enzymes which have a molecular weight of about 250,000 Dalton and a partial amino acid sequence which display [sic] at least 80% homology with SEQ ID NO: 1.

Such endothelin converting enzymes can be isolated from organisms other than cattle, for example from human cells.

The invention furthermore relates to endothelin converting enzymes which comprise the polypeptide sequence described in SEQ ID NO: 30 and SEQ ID NO: 36 or functional fragments thereof.

Functional fragments mean those partial sequences which still have the enzymatic activity of endothelin converting enzyme, the antigenic properties or the affinity for ligands, for example binding proteins.

Other functional fragments are those polypeptide sequences which are obtainable, starting from SEQ ID NO: 30 or NO: 36 by insertion, deletion or substitution of amino acids or peptides and which still have essentially the enzymatic activity of endothelin converting enzymes and/or cross-react immunologically with the endothelin converting enzymes of formula SEQ ID NO: 30 or NO: 36.

The invention furthermore relates to DNA sequences which code for an endothelin converting enzyme and which are selected from the group formed by a) DNA sequences with the structure described in SEQ ID NO: 29 or SEQ ID NO: 35, b) DNA sequences which code for proteins having the structure described in SEQ ID NO: 30 or SEQ ID NO: 36, and c) DNA sequences which hybridize under standard conditions with DNA sequences a) or b), d) DNA sequences which encode protein products which are recognized by antibodies which have been generated against the proteins of SEQ ID NO: 30 or 36 or fragments thereof.

Standard conditions mean, for example, temperatures from 42 to 58° C. in an aqueous buffer solution with a concentration of from 0.1 to 1×SSC (1×SSC: 0.15 M NaCl, 15 mM sodium citrate pH 7.2). The experimental conditions for DNA hybridization are described in textbooks of genetic engineering, for example in Sambrook et al., "Molecular Cloning", Cold Spring Harbor Laboratory, 1989.

The preparation of such DNA sequences is described in Example 8. DNA sequences whose protein products are recognized by antibodies which have been generated against the proteins of SEQ ID NO: 30 or 36 or fragments thereof can be obtained by methods which have been described well.

The raising of antibodies against such proteins is described, for example, in Hudson, L. and Hay, F. C., "Practical Immunology", Blackwell Sci. Pub., Oxford, 1980.

The use of antibodies for finding cDNA sequences which encode proteins cross-reacting with these antibodies is described, for example, in "DNA Cloning Vol. I", Glover, D. M., Ed., IRL Press Oxford, 1985.

The invention furthermore relates to processes for the preparation of endothelin converting enzymes, which comprise mammalian cells, preferably endothelial cells, being stimulated with an inhibitor of endothelin converting enzyme to overproduction of endothelin converting enzyme, and endothelin converting enzyme being isolated from these cells by conventional protein chemical procedures.

All ECE inhibitors can be used for induction of ECE in mammalian cells. ECE inhibitors suitable for this purpose are described, for example, in JP-146737; JP05148277-A1; Jpn J. Biochem. 64; (8) Abst. 2367 (1992); Derwent NCE-93-0956 (1993); Derwent NCE-93-0971 (1993); J. Med. Chem. 36,173 (1993); EP 518299-A2. Phosphoramidon is preferably used. The cells are stimulated in culture by adding these inhibitors to the cell culture medium for 6 hours to 6 days. However, the stimulation is preferably carried out for 2–3 days. The inhibitor concentrations used are from $10^{-2}$ M to $10^{-7}$ M, preferably $10^{-3}$ M to $10^{-4}$ M.

The endothelin converting enzymes according to the invention can, however, also be prepared by genetic engineering means. It is possible on the basis of the described partial amino acid sequences to prepare synthetic oligonucleotides which encode these sequences or are complementary to sequences coding therefor. These oligonucleotides can be used as hybridization probe for isolating corresponding genes or the cDNA molecules from gene pools such as gene banks or cDNA pools. This manner of gene isolation is known to the skilled worker from textbooks of molecular biology such as Sambrook, Fritsch, Maniatis; Molecular Cloning, Cold Spring Harbor Laboratory Press, 1989, U.S.A.

It is likewise possible to obtain parts of the gene, for example from cDNA banks or first strand cDNA using suitable synthetic oligonucleotides and the polymerase chain reaction (PCR) (PCR Protocols; Academic Press; San Diego; U.S.A.; 1990). Oligonucleotides suitable for this purpose can be deduced from the peptides described by Seq ID No. 1 to No. 6 by translating the amino acid sequence into the double-stranded DNA sequence (with sense and antisense). It is possible in this case, because of the degeneracy of the genetic code, for degenerate oligonucleotide mixtures to be derived from one peptide and used as primers. The oligonucleotides can also be derived from the peptides taking account of the codon usage, the preferential use in a species, in this case cattle, of particular nucleotide triplets for an amino acid. The PCR is then carried out with two different oligonucleotides as primers, in which case the two primers necessary for the PCR can be composed of the strand (sense) and complementary strand (antisense) of the oligonucleotides. It is likewise possible to use oligonucleotides which are derived from parts of the cDNA vector, or oligo-dT for the 3' part of mRNA.

These gene parts can then in turn be used in order to obtain by the process of gene isolation the complete gene or the complete cDNA.

It is possible in this way to isolate not only genes for endothelin converting enzymes which have exactly the partial amino acid sequence described in SEQ ID NO:1 but also genes for variants or endothelin converting enzymes from other organisms, for example humans, which display at least 80% homology at the protein level with SEQ ID NO: 1.

The endothelin converting enzymes according to the invention can be prepared particularly well by isolating the corresponding genes and expressing these genes in a host organism using conventional methods of genetic engineering.

The ECE according to the invention or peptides derived therefrom can be used for preparing antibodies or antibody fragments such as $F_v$ fragments, which can be employed, for example, for the determination of ECE, in assay methods for identifying ECE inhibitors or as ECE inhibitors.

Such antibodies are generally valuable aids in the diagnosis of diseases in which endothelin converting enzymes are involved.

It is also possible to use for these purposes PCR primers derived from the DNA sequences according to the invention, in order, for example, to measure the ECE transcription or determine the geno-type.

The resulting genes can be used in a manner known to the skilled worker to modify the complement of genes in animals in such a way that they acquire one or more extra copies of this gene or that the normal ECE gene is switched off. These transgenic animals are suitable, inter alia, for experimental purposes.

Endothelin converting enzymes themselves are also suitable as active ingredient for producing drugs, for example for disorders in which elevated levels of ECE substrates, such as bradykinin, substance P, somatostatin, neuropeptide Y, are present. Examples of such disorders are inflammations, asthma, migraine, rheumatism, cellular processes and cell proliferation taking place with involvement of peptides as growth factors. ECE can also be used as drug for diseases in which vasodilatation which can be eliminated by administration of ECE is present, eg. septic shock, migraine, disturbances of potency.

To use ECE as drug it may be necessary in some circumstances to alter parts of the ECE by mutation. These mutational alterations may lead, for example, to an ECE derivative which is not glycosylated or which contains no membrane anchor (soluble ECE). Such a soluble ECE which no longer contains a membrane anchor can be prepared, for example, by expressing an ECE fragment which contains an extracellular, catalytically active domain. ECE fragments of this type can be obtained, for example, by linking the coding sequence from amino acid 20 to 703 from SEQ ID NO: 25, preferably from amino acid 27 to 703 from SEP[sic] ID NO: 25, to the DNA sequence of a signal peptide which can be eliminated in vivo, and introducing, in a suitable expression vector known to the skilled worker, into eukaryotic cells. An example of a suitable signal peptide is the sequence of human tissue plasminogen activator from amino acid position −35 to −4 (Collen, D., Nature 301, 214 to 221 (1983)). In this connection, alterations may influence, for example, the specificity, the duration of action or the uptake. Furthermore, functional parts of ECE can be coupled to parts of other proteins in order to generate novel proteins which are used as drugs. ECE can also be altered by covalent modification with non-peptide molecules such as PEG, dextran or fatty acids.

The DNA sequences according to the invention are also suitable for use in gene therapy, for example for producing medicines for gene therapy. Diseases with elevated endothelin levels can also be treated with oligonucleotides derived from the ECE DNA sequence. These oligonucleotides are derived from the non-coding DNA strand (antisense) and can be used as drugs. An antisense therapy based on this preferably makes use of more stable chemical derivatives derived from the oligonucleotides. For example, it is possible to use antisense oligonucleotides which are preferably synthesized from the region defined by positions 31 to 100 Seq ID [sic]: 35. The antisense oligonucleotides preferably have a length of from 15 to 30 residues. Antisense therapy or prevention of diseases is used for the same indications as ECE inhibitors, eg. cerebral ischemias; subarrachnoid [sic] hemorrhages; vasospasms; coronary ischemias; disorders associated with cell proliferation processes, such as prostate hyperplasia, such as atherosclerosis, such as restenosis; asthma; hypertension; pulmonary hypertension; organ failure such as heart failure and kidney failure; renal ischemias; neprotoxicity [sic]; myocardial infarct; coronary heart disease; sepsis.

It is also possible to derive from the DNA sequence of ECE sequences with which catalytic RNA molecules can be generated, which are called ribozymes. These catalytic RNA molecules act by cleaving or inactivating, after administration, the ECE RNA or ECE DNA and thus preventing synthesis of ECE protein.

The ECE DNA sequences can be used with suitable expression vectors in order to establish cells which express this enzyme. These cells are used inter alia as drugs.

The endothelin converting enzymes are preferably used in assay methods for identifying ECE inhibitors. These assay methods are, as a rule, enzymatic reactions in which the ECE-catalyzed cleavage of a substrate is measured in the presence of potential inhibitors.

The invention furthermore relates to inhibitors for endothelin converting enzymes which are identified with an enzyme assay using the endothelin converting enzymes according to the invention.

The invention also includes a process for producing drugs which inhibit an endothelin converting enzyme, which comprises employing known chemical compounds in an enzyme assay using the endothelin converting enzymes according to the invention and identifying those with an inhibiting effect, and formulating compounds identified in this way with conventional vehicles and ancillary substances as drugs.

EXAMPLE 1

Stimulation of ECE-1 in FBHE Primary Bovine Endothelial Cells by Phosphoramidon

Three tubes with frozen FBHE bovine endothelial cells (ATCC CRL 1395) were thawed in the 14th passage and introduced into 3 T175 cell culture bottles (from Sarstedt) each containing 40 ml of DMEM growth medium (Gibco No. 041-01965).

+5 ml/500 ml glutamine (200 mM; Gibco 043-05030)
+1 ml/500 ml gentamicin (Gibco 043-05750)
+non-essential amino acids; final concentration: 1×(Gibco No. 043-01140)
+10% FCS (Gibco No. 011-06290; inactivated for 37 minutes at 56° C.)+25 ng/ml basic FGF (Intergen 4125-80)).

These cells were incubated by standard methods at 37° C. in an atmosphere of 7% $CO_2$, 100% humidity. The medium was changed the next day. When confluence was reached, in this case after 4 days, the cells were passaged in accordance with standard methods by trypsin treatment, and distributed into 9 T-175 bottles and incubated at 37° C. for growth as described. After confluence was reached after 3 days, the cells were again distributed to 20 T bottles in accordance with standard methods by trypsin treatment. After a further 3 days it was possible to distribute the cells to 40 T bottles. After a further 3 days, 39 of these T bottles were distributed to 78 T bottles. Since these 78 T bottles are used to harvest the cells, suitable cell culture bottles (from Costar; Accell; No. 3155) are used for this purpose. On the day after inoculation of these T bottles, phosphoramidon (from Peptide Institute; No. 4082; abbreviated to PHAM) was added in a final concentration of $10^{-4}$ M to 68 bottles (+PHAM). This treatment leads to induction of ECE activity. The remaining 10 T bottles were included as non-induced control cells (−PHAM). After incubation under the described conditions for a further 2 days, the PHAM-induced cells and the control cells (−PHAM) were harvested separately. This was done by opening the bottles and tipping out the medium. The cells were washed in the T bottle with 10 ml of PBS (Boehringer Mannheim No. 210331) in each case (ie. cautiously swirled over the cell lawn). The PBS was tipped out. 5 ml of PBS were again added to each T bottle. The cells were scraped off the bottom of the culture bottle using a cell scraper (from Costar No. 3010) and transferred as cell suspension into a 150 ml centrifuge tube (Falcon No. 2076), where they were stored on ice. Each T bottle was then rinsed with 10 ml of PBS. The cell suspension from the rinsing was combined with the cell suspension present in the centrifuge tubes. The cells were sedimented by centrifugation (1200 rpm; 10 minutes; Heraeus Christ Minifuge GL No. 4400; Rotor 2150). The cell-free supernatant was discarded, and the pellet was taken up in PBS in 3 times the volume of the cell sediment. After centrifugation again, the cell-free supernatant was again discarded. The pellet remained on ice until worked up.

EXAMPLE 2

Comparative enrichment of non-stimulated and phosphoramides-stimulated [sic] FBHE bovine endothelial cells; identification of the protein.

The FBHE cells obtained in Example 1 with and without phosphoramidon induction (in each case 500 µl of moist mass) were treated with ultrasound in 15 ml of PBS buffer, 0.5 mM diisopropyl fluorophosphate in an icebath for 20 minutes. After centrifugation (1000 g, 20 min), the membranes were precipitated by adding 5% Pluriol F68® to the supernatant and were obtained by centrifuging again at 10,000 g. The membranes were digested with 2 ml of 100 mM Tris buffer, pH 8.0, and solubilized with 1% Triton X-100®. The solubilisates (2.5 ml each) were centrifuged, and the residues were discarded.

Mono-Q® Chromatography

The solubilisates of the ±phosphoramidon-induced cells were chromatographed separately on a Mono Q® HR 5/5 column (from Pharmacia) under exactly identical conditions. The column is equilibrated with 50 ml of Tris buffer, pH 8.0, 0.1% Triton X-100 (A buffer). The solubilisate is loaded on and then washed with A buffer for 15 min, and a linear gradient with B buffer (A buffer+1 M NaCl is run for 50 min (flow rate 0.2 ml/min). 20 fractions of 0.5 ml are collected and assayed with human big Et-1 as substrate. The Et-1 which is produced is detected and quantified by reversed phase HPLC in the manner described (Example 3). The two fractions with the highest enzyme activity are combined in each case.

Superose 12® Gel Chromatography

The eluates from the Mono Q chromatographies are concentrated to 250 μl using Centricon® tubes (from Amicon) and, in each case, subjected to gel chromatography on Superose 12 HR10/36.

| Conditions: | Buffer: | 20 mM sodium phosphate, 250 mM NaCl, pH 7.4, 0.05% Triton × 100 |
| --- | --- | --- |
| | Flow rate: | 0.5 ml/min |
| | Fraction: | 0.5 ml |

The fractions are assayed by the assay described in Example 3, and in each case the two fractions with the highest enzyme activity are combined.

Protein was determined in all fractions by the method of Bradford (Anal. Biochem. 72, 248 (1976)).

Results

The purification of stimulated and unstimulated cells gave the following results at the various purification stages:

| Purification step | Spec. act. [μU/mg] FBHE cells + phosphoramidon | μg/mg FBHE cells − phosphoramidon |
| --- | --- | --- |
| Membranes | 129 | 44 |
| Solubilisate | 188 | 22 |
| Mono Q chromat. | 1470 | 78 |
| Superose 12 chromat. | 4500 | 130 |

The two active fractions from the Superose 12® chromatography were loaded onto an 8% SDS polyacrylamide gel for comparison. The gel pattern of purified ECE-1 from phosphoramidon-treated cells shows an additional band at 250,000 Dalton when compared with untreated cells. When the proteins are loaded on with the reducing agent dithiothreitol (DTT), comparison shows an additional band at 125,000 Dalton.

EXAMPLE 3

ECE-1 Activity Assay by HPLC

Conversion of big endothelin-1 into endothelin-1 by endothelin converting enzyme (ECE-1)

1 μl of enzyme solution obtained as in Example 4 was mixed with 21 μl of 50 mM Tris, 50 mM imidazole, 250 mM NaCl, pH 7.4 buffer and 2.5 μl of human big endothelin (2 mg/ml in 0.1% acetic acid in water). After 2 hours, the reaction was stopped with 72 μl of 0.5% trifluoroacetic acid in order to analyze the endothelin produced. The sample was centrifuged and the supernatant was identified and, by comparison with an endothelin standard, quantified by reversed phase high pressure liquid chromatography (RP-HPLC) analysis with UV detection (205 nm) as described in (J. Takada et al., Biochem. Biophys. Res. Comm. 176, 860 (1991), K. Ohnaka et al., Biochem. Biophys. Res. Comm. 168, 1128 (1990)).

The enzyme activity can then be calculated in activity $$ECE[\mu U] = \frac{10^{-6} \mu M \text{ endothelin}}{\min}$$

This method was used to determine the ECE activity at various stages in the purification from the workup of FBHE cells. At the same time, the amounts of protein were determined by the method of Bradford (Anal. Biochem. 72, 248 (1976)).

EXAMPLE 4

Purification of ECE-1 from FBHE Bovine Endothelial Cells a) Obtaining membranes, trypsinization of foreign protein 6 ml of FBHE cell pellet (from Example 1) are digested in 25 ml of PBS buffer and disrupted in an ultrasound bath while cooling in ice for 15 minutes. The cell detritus was removed by centrifugation at 10,000 g for 20 min. 3.6 mg of trypsin were added to the supernatant while stirring, and the mixture was stirred at room temperature for 1.5 h. The sample was centrifuged at 100,000 g for 1 h, and the membranes present in the residue were suspended with 25 ml of 100 mM Tris buffer, pH 8.0.

b) Solubilization of ECE-1

The 25 ml of membrane suspension was adjusted to 0.5 mM diisopropyl fluorophosphate and then 0.5% Triton X-100® and stored in an icebath overnight.

c) Mono-Q® chromatography

A Mono-Q® FPLC column, HR16/10, from Pharmacia was equilibrated with 50 mM Tris buffer, pH 8.0; 0.05% Triton X 100® (A buffer).

The solubilisate was loaded on and then washed with A buffer for 30 min, and elution was subsequently carried out with a linear gradient to buffer B (buffer A+1 m NaCl) over the course of 100 minutes. 30 fractions of 10 ml each are collected. The protein content of the samples is determined by the Bradford method, and the ECE-1 activity is determined as in Example 3.

The two fractions with the highest specific activity were combined.

d) Gel filtration

The combined Mono-Q® eluates from 4c) were concentrated to 500 μl through a 30 KDa Centricon membrane (from Amicon).

A Superose 12® HR 10/30 column (from Pharmacia) is equilibrated with 20 mM Na phosphate buffer, pH 7.4, 250 mM NaCl, 0.05% Triton X-100, and the concentrated sample is loaded on. Chromatography is carried out with the equilibration buffer at a flow rate of 0.5 ml [sic], and 0.5 ml fractions are collected.

The specific activity of the fractions is determined as in 4c). The fraction with the highest specific activity is indicated under e); it elutes at about 250,000 Dalton, using standard proteins for calibration under identical chromatography conditions.

e) Results

| Purification step | Protein [mg] | Spec. activity [μU/mg] |
| --- | --- | --- |
| Membranes | 87 | 410 |
| Solubilisate | 87 | 360 |
| Mono Q eluate | 6.6 | 3760 |
| Superose 12 eluate | 0.35 | 15100 |

EXAMPLE 5

SDS Gel Analysis of Purified ECE-1 from FBHE Cells

The ECE-1 purified in Example 4 is analyzed on an 8% SDS gel by the method of Lämmli (Nature 227, 680 (1979)) under non-reducing and reducing conditions (+DTT). This shows that ECE-1 has a molecular weight of 250,000 Dalton in the non-reduced state and, after reduction, disintegrates into a broad band around 125,000 Dalton.

EXAMPLE 6
Deglycosylation of ECE-1

50 µl of the ECE-1 solution purified in Example 4 were adjusted to an SDS content of 0.25% with 10% strength SDS solution. The samples were incubated at room temperature for 20 min and adjusted to 1% Triton X-100. After 20 min at RT, 5 µl of 250 mM Na phosphate buffer, pH 4.7, were added. Then 0.25 µl of PNGase and 0.5 µg of Endo F were added. The samples were incubated at 37° C. for 8 h. The same amounts of enzymes were then again added and incubation was continued at 37° C. for 8 hours. The samples were then concentrated to 50 µl and analyzed in a 4–12% SDS gel.

Results

In the reduced state, the apparent molecular weight of 125,000 Dalton is altered by elimination of the sugar residues with the PNGase F/Endo F mixture to about 82,000 Dalton.

EXAMPLE 7
Partial Sequences of the ECE-1 from Bovine Endothelial Cells

16×25 µg of the ECE-1 solution obtained in Example 4 were loaded onto preparative 4–12% SDS polyacrylamide gradient gels. After conventional staining with Coomassie blue, the gel is destained and hydrated in pure water for 4×40 minutes. The stained bands at 250 KDa were cut out with a scalpel and digested with 200 µl of 100 mM NH$_4$HCO$_3$ solution. 0.5 µg of trypsin is added and the mixture is incubated overnight, and the supernatant is then removed. The residue is again incubated with 0.5 µg of trypsin in 200 µl of 100 mM NH$_4$HCO$_3$ buffer at room temperature for 5 h. The sample is then concentrated to dryness in a speed-vac concentrator. The residue is taken up in 40 µl of water and stirred with 4 µl of 40 mM dithiothreitol solution for 30 min. Then, at 37° C., 4 µl of 100 mM iodoacetamide solution were added. After 2 hours, the sample is concentrated to dryness.

The resulting peptides were fractionated on a 1 mm×15 cm reversed phase HPLC column in a linear gradient from 0.5% trifluoroacetic acid in water to 0.5% trifluoroacetic acid in 90% acetonitrile in 3 hours. UV-active fractions were collected, and the primary sequences were determined in a gas phase sequencer.

Results

The following partial sequences were determined:

```
SEQ ID NO: 1:

Xaa-Xaa-Pro-Asn-Ala-Leu-Asn-Phe-Gly-Gly-Ile-Gly-Val-
Val-Val-Gly-His-Glu-Leu-Thr-His-Ala-Phe . . .

SEQ ID NO: 2:

Xaa-Tyr-Xaa-Lys-Xaa-Gly-Asn-Leu-Arg-Pro

SEQ ID NO: 3:

Xaa-Ile-Ala-Xaa-Glu-Thr-Glu-Leu-Glu-Ile . . .
                         (Ile)(Ile)

SEQ ID NO: 4:

Xaa-Pro-Glu-Phe-Leu-Leu-Glu-Gly-Leu-Ile-Thr-Asp-Pro . . .

SEQ ID NO: 5:

Xaa-(Gln)-(Ala)-(Glu)-Asn-Val-Ile-Gln-Val-Xaa-Gln . . .

SEQ ID NO: 6:

Val-Glu-Ile-Val-Phe-Pro-Ala-Gly-Ile-Leu-Gln-Ala-Pro-(Phe)-Tyr-Thr
                                                     (Thr)
```

The amino acids indicated in parentheses were not identified with absolute certainty.

SEQ ID NO: 1 proves that ECE-1 is a novel protein from the metalloprotease family because, on comparison with sequences of the metalloendopeptidases NEP 24.11 and thermolysin, it shows significant homologies of 72% and 40% respectively.

EXAMPLE 8
Preparation of a cDNA Sequence Coding for an Endothelin Converting Enzyme a) Isolation of RNA and preparation of a cDNA bank Complete RNA from FBHE cells which have been stimulated with phosphoramidon as in Example 1, or from HeLa cells which have been stimulated with phosphoramidon as in Example 1, was obtained by disruption in guanidinium thiocyanate. This was done using the materials in accordance with the instructions in the RNA isolation kit supplied by Stratagene, La Jolla, Calif., U.S.A. (Catalog No. 200345).

The polyadenylated messenger RNA was selected from the abovementioned complete RNA from FBHE cells by oligo(dT) affinity separation. This method was carried out with materials and in accordance with the instructions of the PolyATtract mRNA Isolation System supplied by Promega, Madison, Wis., U.S.A. (Catalog No. Z5200). cDNA was synthesized from polyadenylated messenger RNA using materials and in accordance with the instructions of the ZAP-cDNA synthesis kit supplied by Stratagene, La Jolla, Calif., U.S.A. (Catalog No. 200400) and was then packaged in lambda phages using materials and in accordance with the instructions of the Uni-ZAP XR GigapackII cloning kit supplied by Stratagene, La Jolla, Calif., U.S.A. (Catalog No. 237611).

b) Preparation of oligonucleotide probes for the RACE PCR

The peptides indicated in Example 7 with SEQ ID NO:1 and NO:6 were the starting point for the cloning of cDNA fragments by the polymerase chain reaction (PCR, see Molecular Cloning, 2nd Edition (1989), Sambrook, J. et al., CSH Press, page 14.1 et seq.).

On the basis of the genetic code it is possible to deduce from SEQ ID NO: 1, position 16 to 22, an oligonucleotide mixture with nucleic acid sequence SEQ ID NO:7:

5'-GGSCAYGARYTNACNCAYGC-3'.

It is likewise possible to deduce from SEQ ID NO: 6, position 2 to 8, an oligonucleotide mixture with SEQ ID NO: 8:

5'-GARATYGTSTTYCCYGCYGG-3', and from SEQ ID NO: 6, position 9 to 16 an oligonucleotide mixture with SEQ ID NO: 9:

5'-ATYCTSCAGGCYCCYTTYTAYAC-3'.

In this case, SEQ ID NO: 7 to NO: 9 correspond to the sequence of the coding DNA strand. Several nucleotides have been inserted at some positions because of the known degeneracy of the genetic code. This results in an up to 512-fold complexity of the mixture for SEQ ID NO: 7 to 9. Said sequences were synthesized as oligonucleotides.

The following oligonucleotides were additionally synthesized as 3' primers in the RACE PCR:

A-B-T18 (SEQ ID NO: 10):

5'-CGAGGGGGATGGTCGACGGAAGCGACCTTT TTTTTTTTTTTTTT-3'; and

A (from A-B-T18) (SEQ ID NO: 11):

5'-CGAGGGGGATGGTCGACGG-3'; and

B (from A-B-T18) (SEQ ID NO: 12):

5'-GATGGTCGACGGAAGCGACC-3'.

The syntheses were carried out using an Applied Biosystems Type 360A DNA synthesizer. The oligonucleotides were, after removal of the protective groups, purified by gel electrophoresis on an acrylamide/urea gel.

c) Preparation of DNA templates for the PCR

5 μg of complete RNA or 1 μg of poly(A)+RNA of the RNA preparation mentioned under a) from phosphoramidon-stimulated FBHE cells were translated into single stranded cDNA (sscDNA) with 1 μg of the oligonucleotide A-B-T18 (SEQ ID NO: 10) and using the reverse transcriptase enzyme. This was done using materials and in accordance with the instructions of the Superscript Preamplification System supplied by Gibco BRL, Eggenstein, Germany (Catalog No. 8089SA). After the reaction was complete, the synthesized products were purified using the Geneclean II kit supplied by BIO 101, La Jolla, Calif., U.S.A., to remove smaller molecules and excess oligonucleotides.

d) PCRs and cloning of a part cDNA sequence

The polymerase chain reaction was carried out by known protocols (see Molecular Cloning, 2nd Edition (1989), Sambrook, J. et al., CSH Press, Page 14.1 et seq.). A DNA Thermal Cycler supplied by Perkin Elmer was used for this. Also used were the principle of "internal primers" of Frohmann, M. A. et al. (Proc. Natl. Acad. Sci. U.S.A. (1988) 85, 8998–9002) and a modification of the method of Fritz, J. D. et al. (Nucl. Acids Res. (1991) 19, 3747).

Specifically, the sscDNA from c) was amplified with, in each case, 20 pmol of the oligonucleotides SEQ ID NO: 8 and A (from A-B-T18). The conditions for this were: 1' 95° C.; 2' 55° C.; 3' 72° C. for 35 cycles.

The PCR products were fractionated by electrophoresis on a 1.2% LMP agarose/TBE gel.

About 10 gel disks were cut out of the gel over the entire length of the "tail", and these were melted as separate fractions with DNA fragments of increasing molecular weight.

Aliquots of these fractions were then employed separately in a second PCR with, in each case, 20 pmol of the oligonucleotides SEQ ID NO: 9 and B (from A-B-T18). During this the agarose content never exceeded 1/10 of the volume of the PCR mixture. Reaction conditions: 1' 95° C.; 2' 50° C.; 3' 72° C. for 35 cycles.

Fractionation by gel electrophoresis of the amplification products of these fractions clearly revealed a reduction in the complex product spectrum of the first PCR to a defined band with a length of about 1000 bp after the second PCR.

This PCR product selected in this way was eluted by standard methods. The identity of the band 1000 bp in size as a fragment of bovine endothelin converting enzyme cDNA was first checked by another, third PCR amplification using the oligonucleotides SEQ ID NO: 7 and B (from A-B-T18). The product of this PCR was a band about 950 bp in size.

After subcloning of the band 1000 bp in size from the second PCR reaction into the vector pCR II (TA Cloning Kit, Invitrogen Corp., San Diego Cat. No. K2000-01) and replication of the plasmid in E. coli DH5alpha, sequence analysis of a clone revealed an open reading frame of 189 amino acids SEQ ID NO: 13, NO: 14). The sequences for the peptide SEQ ID NO: 1, NO: 2 and NO:4 were also located in the same reading frame, which unambiguously defines the identity of the cDNA fragment.

e) Cloning of a bovine cDNA for endothelin converting enzyme

The protocol detailed in Example 1a) [sic] was used to generate a cDNA library with a random primer mixture at the step of synthesis of the first strand. The primers were synthesized as the sequence:

5'-GAGAGAGAGTCGACGGTACCN7; SEQ ID NO: 15.

As a deviation from the abovementioned cDNA synthesis protocol, the double-stranded cDNA was fractionated on a 2 ml Sephacryl S-1000 (grade: superfine; Pharmacia, Freiburg; Catalog No. 17-0476-01) column. The fractions with cDNA fragments at least 1 kb in size were concentrated by alcohol precipitation in a conventional way and subsequently treated in accordance with the instructions in the cDNA synthesis kit, with the cDNA preparation subsequently being cleaved with the restriction endonuclease SalI in place of XhoI and being integrated into the lambda vector.

2×106 [sic] clones from the bank were hybridized, after transfer to nylon membranes, with a DNA probe which was produced using the oligonucleotides 5'-CGGCCCTGGTGGAAGAACTCG-3' (SEQ ID NO: 16) and

5'-TGCGGACGGAACACCAGACCT-3' (SEQ ID NO: 17)

from the partial bovine cDNA (SEQ ID NO:13), position 136 to 156, and 391 to 412 respectively. The DNA probe was labeled in a polymerase chain reaction (PCR) in the presence of digoxigenin-dUTP as described in Example 1f) [sic]. The hybridization was carried out under stringent conditions (see Example 1f) [sic]), the last washing step being carried out after hybridization in 0.1×SSC, 60° C., and subsequently the bound DNA probe being detected immunologically. Sequencing of selected clones revealed the bovine cDNA sequence C60, SEQ ID NO: 18, with a continuous reading frame, SEQ ID NO: 19.

Then 2×106 [sic] clones from the bank were hybridized with a DNA probe which was generated using the oligonucleotides 5'-GCCAGCGCCGTCTCAAAGTCCAG-3' (SEQ ID NO: 20) and 5'-TGGGGGACCTTCAGCAACCTCT-3' (SEQ ID NO: 21)
from the cDNA clone C60, SEQ ID NO: 18, position 500 to 522, and 14 to 35 respectively, as described above, under identical conditions. Sequencing of selected clones revealed the bovine cDNA sequence SEQ ID NO: 22 with a continuous reading frame of 708 amino acids (SEQ ID NO: 23).

5×108 [sic] plaque-forming units of a commercial bovine lung cDNA bank in lambda gt11 (Clontech Laboratories, Inc.; 4030 Fabian Way; Palo Alto Calif. 94303-4607, U.S.A.; Catalog No. BL1006b) were concentrated by precipitation with 10% polyethylene glycol 6000, 1 M NaCl resuspended in 100 µl of double-distilled water and heated at 70° C. for 5 min. 5 µl of this lysate were used in a 50 µl standard PCR reaction (Example 8d) with the primers gt11 fwd and 5'-GGTGCTTGATGATGGCTTGGTTGT-3' (SEQ ID NO: 26). The primer gt11 fwd corresponds to position 2979–3003 of the β-galactosidase gene (gene bank: ECLACZ) and is located in the lambda gt11 cloning vector directly in front of the unique EcoRI integration site which was used for constructing the bank (Young, R. A. &. Davis, R. W. (1985) Genetic Engineering, Ed. by Setlow, J. U. Hollander, A. Plenum Press, New York 29–41). The primer SEQ ID NO: 26 corresponds to position 280–303 of SEQ ID NO: 22.

The amplifications were carried out over 40 cycles. The PCR product was fractionated on a 3% low melting point Nu-Sieve GTG agarose gel (supplied by FMC BioProducts, 191 Thomaston Street, Rockland, Me. 04841, U.S.A.; Catalog No. 50082), and the size range of 400–600 base pairs was fractionated by cutting out individual gel segments. The gel disks were melted as described in Example 8d), and 1.5 µl were used in 50 µl of a fresh PCR reaction with the primers gt11 fwd and 5'-AGATGGAGCTGGTCACCGAGATGC-3' (SEQ ID NO: 27). The primer SEQ ID NO: 27 corresponds to position 127–150 of SEQ ID NO: 22.

The resulting PCR fragments were sequenced after subcloning in the plasmid vector pUC18 (Yanisch-Perron, D., Vieira J. & Messing, J. (1985) Gene 33, 103–119) (SEQ ID NO: 28).

This sequence overlaps, with nucleotides 175–324, positions 1–150 in SEQ ID NO: 22 and extends it by 174 nucleotides in the 5' direction. The resulting complete sequence (SEQ ID NO: 29) encodes an open reading frame of 754 amino acids (SEQ ID NO: 30).

f) Cloning of a human cDNA for endothelin converting enzyme

Since endothelin-1 has been detected in human placenta, it was assumed that endothelin converting enzyme is also expressed in placenta. Hence a labeled bovine cDNA probe was used to screen a human λgt-11 placental cDNA bank. To prepare the bovine cDNA probe labeled with digoxigenin-dUTP, 1 ng (1 ng/ml) of the partial bovine cDNA sequence (SEQ ID NO: 13) was used as template in a PCR reaction (see Molecular Cloning, 2nd Edition (1989), Sambrook, J. et al., CSH Press, page 14.1 et seq.). The sense oligonucleotide (SEQ ID NO: 16) comprised the nucleotides from position 136 to 156 in SEQ ID NO: 13, while the antisense oligonucleotide SEQ ID NO: 17) comprised positions 392 to 412 in SEQ ID NO: 13. The following cycles were carried out 35 times in the DNA Thermal Cycler (Perkin Elmer): 2 min at 94° C., 2 min at 60° C. and 3 min at 72° C. The labeled 276 bp bovine cDNA probe was subsequently purified on an agarose gel and denatured by boiling. This probe was used to screen, under low stringency conditions, about 650,000 clones of a human placental λgt-11 cDNA bank (Clontech, HL 1008b). Hybridization of the filter extracts with the probe took place in 5×SSC, 2% blocking reagent (Boehringer Mannheim; No. 1096176), 0.1% N-laurylsarcosine, 0.02% SDS at 60° C. overnight. The filters were then washed 2×5 min at 60° C. with 2×SSC, 0.1% SDS and subsequently for 20 min at 60° C. with 0.5×SSC, 0.1% SDS. Further development of the filters for identification of the bound DIG probes took place in accordance with the Boehringer Mannheim protocol (DIG nucleic acid dedection [sic] kit No. 1175041).

Clones with the cDNA sequence indicated in SEQ ID NO: 24 were isolated. The nucleotides in position 1 to position 2109 of the cDNA sequence with SEQ ID NO: 24 code for the amino acid sequence indicated in SEQ ID NO: 25. The amino acid sequence corresponds to the major part of the primary sequence of endothelin converting enzyme because the peptides SEQ ID NO: 1 to SEQ ID NO: 6 from the trypsin peptide sequencing of the isolated endothelin converting enzyme are found in the sequence. It is also possible to identify the metalloprotease concensus sequence HEXXH as HELTH in positions 540 to 544 in amino acid sequence SEQ ID NO: 25.

A cDNA library was generated from 3 µg of placental poly A(+) RNA as described in Example 8e) using the oligonucleotide 5'-GAGAGAGAGAGAGAGAGAGAAC-TAGTC TCGAGCCAAGCAGGCCACCAGTCCTG-3 (SEQ ID NO: 31) as first strand cDNA synthesis primer. Nucleotides 32 to 53 correspond to positions 32 to 53 in SEQ ID NO: 24. The cDNA preparation was integrated as described in Example 8a) into the lambda vector Uni-ZAP XR. The resulting 4×105 [sic] independent clones were amplified, and 5×108 [sic] plaque-forming units were used in a 100 µl PCR reaction as described in Example 8e). The primers SEQ ID NO: 31 and C were used for this. Primer C is located in the lambda vector in the Bluescript SK(−) part, Pos. 881–904, sequence file gene bank: ARBLSKM.

The PCR reaction was carried out for 40 cycles at a hybridization temperature of 65° C. 1 µl of the reaction product was added to a fresh 50 µl PCR reaction mixture, which underwent 40 cycles at a hybridization temperature of 60° C. The primers used were oligonucleotides D and

5'-CCTGCCGCCAGAAGTACCACCAACA-3' (SEQ ID NO: 32).

Primer D is located in the Bluescript SK(−) part of the lambda Uni-ZAP XR vector (Pos. 857–880, sequence file gene bank: ARBLSKM), and the primer SEQ ID NO: 32 corresponds to position 11–35 in SEQ ID NO: 24. The reaction product was subcloned in the plasmid vector pUC18 as described above. Selected clones were sequenced.

The sequence obtained was a novel 5' portion of the human ECE cDNA (SEQ ID NO: 33, whose 3' terminal region (Pos. 188–222) lock-forms with position 1–35 in SEQ ID NO: 24. It extends it by 187 nucleotides in the 5' direction and provides the complete human ECE sequence SEQ ID NO: 35 which encodes an open reading frame of 753 amino acids (SEQ ID NO: 36).

EXAMPLE 9

Preparation of Recombinant ECE in Mammalian Cells

1. Construction of an expression vector of membrane-bound human ECE

For expression of the complete human ECE, the cDNA sequence (SEQ ID NO: 35) from nucleotide 29 to 2720 was inserted with suitable adaptors into the expression vector pcDNA3neo supplied by Invitrogen (3985 B Sorrento Valley Blvd., San Diego, Calif. 92121, U.S.A.; product No. V790-20) between the Kpn I and Xba I restriction sites. The ECE sequence provides its own translation start and stop sequences and a consensus Kozak sequence (Kozak, M. (1989) J. Cell Biol. 108, 229–241). In this vector, transcription of the ECE messenger RNA is under the control of the strong cytomegalovirus promoter. Selection of transfected cells is carried out via the neomycin resistance gene which is located in the plasmid and permits only G418-resistant colonies to grow.

2. Construction of an expression system for secreted human ECE a) The cloning was carried out in a commercially obtainable eukaryotic expression vector pcDNA3neo supplied by Invitrogen (3985 B Sorrento Valley Blvd., San Diego, Calif. 92121, U.S.A.; product No. V790-20). For this, the vector was initially cleaved with the restriction enzymes Eco RI and Eco RV.

b) Then the nucleic acid fragment position 241-position 2396 from the cDNA of human ECE (SEQ ID NO: 35) was obtained by a polymerase chain reaction with suitable oligonucleotide primers. Owing to the choice of the sequence of the 5' primer, the nucleic acid sequence between position 241 and position 245 (SEQ ID NO: 35) was altered in the base sequence 5'-ACGCG-3'. By inclusion of position 246, this step generated a recognition sequence for the restriction endonuclease Mlu I. The resulting ECE fragment was cleaved with Mlu I in a further step.

c) As further fragment, the coding sequence of human tissue plasminogen activator (t-PA) between nucleotide 74 and nucleotide 176 of the published sequence (D. Collen, Nature 301, 214–221 (1983)) was prepared from two synthetic oligonucleotides (strand/complementary strand). In addition to the stated sequence, the synthetic oligonucleotides were provided with adapters which lead to a 5' Eco RI and 3' Mlu I protrusion.

Ligation of the fragments generated in b) and c) via the common Mlu I restriction cleavage site leads to fusion of the reading frames of the signal peptide of the human t-PA gene and of the extracellular domain of the human ECE gene. Ligation of this fusion product into the pcDNA3 vector from a), which had been cut with Eco RI and Eco RV, leads to an expression system for secreted human ECE.

Expression in mammalian cells

The DNA of the expression vectors was transfected into mammalian cells using Lipofectamine (Gibco; Life Technologies GmbH; Dieselstraβe 5, 76334 Eggenstein, Germany; No. 530-8324SA). The cells used were CHO-K1 (ATCC CCL 61); BHK-21 (ATCC CCL 10); 293 (ATCC CRL 1573) and C127I (ATCC CRL 1616).

$2 \times 10^5$ cells in each case were introduced into 3 ml of growth medium in each well of a 6-well culture plate. The transfection was carried out the next day. To do this, the cells were washed once with PBS. The transfection with Lipofectamine was carried out in accordance with the information provided by the manufacturer Gibco (Focus (1993), 15 No. 3, 73–78). Each well received 1 µg of DNA and 6 µl of Lipofectamine, which were together applied in 1000 µl of serum-free cell culture medium. After incubation at 37° C. for 6 hours, the cells were washed once with PBS and incubated with normal growth medium overnight. The next day, the cells in a well were detached using trypsin and then distributed to 1, 5 or 10 Petri dishes (10 cm diameter). The following day the transfected cells were selected by treatment with G418 (Gibco; Cat. No. 066-01811Y; tradename: Geneticin), ie. the growth medium was replaced by a medium containing 1.2 mg/ml G418. After 7–10 days, colonies of G418-resistant cells were to be seen in the Petri dishes. These were isolated by the cloning cylinder method (DNA Cloning Vol. II; Ed. D. M. Glover, IRL Press, 1985; page 220). The isolated colonies were each placed in one well of a 24-well dish with about 1.5 ml of growth medium (including G418). When confluence was reached, the cells were transferred by trypsinization into larger culture vessels.

a) Membrane-bound ECE

Cells which expressed membrane-bound ECE were investigated for the presence of ECE after cell disruption and fractionation as described in Example 1 and 2. (No phosphoramidon stimulation was carried out.) The specific activity of the analyzed colonies was up to 1550 µU/mg of protein based on membranes. Membranes of colony 38 were worked up further. The result of this was as follows:

| Purification step | Spec. activity (µU/mg protein) |
| --- | --- |
| Membranes | 1550 |
| Solubilisate | 2010 |
| Mono-Q chromatography | 12000 | b) Secreted ECE

Cells which express the ECE without membrane anchor and secrete it into the cell culture medium were assayed for the presence of the recombinant ECE by investigating the cell culture supernatant from confluent cells for ECE activity. For this purpose, the cell culture supernatant was removed after a cultivation time of 2 days, and cell detritus was removed by centrifugation at 1000 g. 6 ml of the supernatant were then concentrated using a Centricon 10,000 (Amicon, W. R. Grace+Co., Danver, Mass. 01923, U.S.A.; product No. 4206) and centrifugation at 3220 g (about 30 min). The liquid containing the low molecular weight substances which had flowed through was kept (Centricon eluate). The Centricon was washed once with 1 ml of PBS+10 mM Tris+150 mM NaCl; pH 7.5. The concentrate was taken up in 300 µl of the Centricon eluate. 18 µl of the concentrate were used in the ECE assay as described in Example 3.

The volume-based activity of the secreted ECE was up to 10 µunits/ml of cell culture medium, depending on the colony of recombinant cells investigated.

What is claimed is:

1. An isolated endothelin converting enzyme having an amino acid sequence described in SEQ ID NO: 36.

2. An isolated DNA encoding an endothelin converting enzyme defined in claim 1 and having a nucleotide sequence shown in SEQ ID NO: 35.

3. A method of expressing a DNA having a sequence encoding endothelin converting enzyme with an amino acid sequence shown in SEQ ID NO: 36, which method comprises (a) isolating a DNA sequence which hybridizes under stringent conditions with a probe consisting of a DNA fragment of SEQ ID NO: 36, or a sequence-complementary DNA fragment;

(b) ligating said DNA sequence to an expression vector and introducing said vector into a host cell; and (c) measuring the endothelin converting enzyme activity of the transformed cell.

4. A method of identifying an inhibitor of endothelin converting enzyme, which method comprises exposing a substrate to the endothelin converting enzyme defined in claim 1 in the presence of a possible inhibitor, and inspecting the substrate for cleavage; wherein an inhibitor of endothelin converting enzyme is positively identified when the substrate is cleaved.

* * * * *